(12) United States Patent
Kweon et al.

(10) Patent No.: US 11,103,539 B2
(45) Date of Patent: Aug. 31, 2021

(54) PHARMACEUTICAL COMPOSITION FOR PREVENTING OR TREATING METABOLIC DISEASES, COMPRISING BACTEROIDES ACIDIFACIENS AS ACTIVE INGREDIENT

(71) Applicant: GI BIOME, Seoul (KR)

(72) Inventors: Mi Na Kweon, Seoul (KR); Jin Young Yang, Seoul (KR)

(73) Assignee: GI BIOME, Seoul (KR)

( * ) Notice: Subject to any disclaimer, the term of this patent is extended or adjusted under 35 U.S.C. 154(b) by 0 days.

(21) Appl. No.: 16/443,501

(22) Filed: Jun. 17, 2019

(65) Prior Publication Data

US 2019/0328797 A1 Oct. 31, 2019

Related U.S. Application Data

(63) Continuation of application No. 15/534,068, filed as application No. PCT/KR2015/013402 on Dec. 8, 2015, now Pat. No. 10,369,174.

(30) Foreign Application Priority Data

Dec. 8, 2014 (KR) ........................ 10-2014-0175349

(51) Int. Cl.
| | |
|---|---|
| A61K 35/74 | (2015.01) |
| A61K 38/17 | (2006.01) |
| A61K 35/66 | (2015.01) |
| A23L 33/00 | (2016.01) |
| A23L 33/135 | (2016.01) |
| A61K 45/06 | (2006.01) |
| C12N 5/0784 | (2010.01) |

(52) U.S. Cl.
CPC ............ *A61K 35/74* (2013.01); *A23L 33/135* (2016.08); *A23L 33/30* (2016.08); *A23L 33/40* (2016.08); *A61K 35/66* (2013.01); *A61K 38/1709* (2013.01); *A61K 45/06* (2013.01); *C12N 5/0639* (2013.01); *A23V 2002/00* (2013.01); *C12N 2510/00* (2013.01)

(58) Field of Classification Search
None
See application file for complete search history.

(56) References Cited

U.S. PATENT DOCUMENTS

| 9,061,001 | B2 | 6/2015 | Van Drunen Littel-Van Den Hurk et al. |
|---|---|---|---|
| 9,408,908 | B2 | 8/2016 | Van Den Hurk et al. |
| 9,758,527 | B2 | 9/2017 | Yang et al. |
| 9,783,592 | B2 | 10/2017 | Dimarchi et al. |
| 10,169,541 | B2 * | 1/2019 | Apte .................. G06F 19/3418 |
| 10,300,085 | B2 * | 5/2019 | Shimamoto ............ A61P 35/00 |
| 10,369,174 | B2 * | 8/2019 | Kweon .................. A23L 33/30 |
| 10,381,112 | B2 * | 8/2019 | Apte ...................... G16H 10/40 |
| 10,485,830 | B2 * | 11/2019 | Jeffery .................... A61P 29/00 |
| 10,633,714 | B2 * | 4/2020 | Cutcliffe ................ C12Q 1/689 |
| 2014/0045744 | A1 | 2/2014 | Gordon et al. |
| 2016/0235792 | A1 | 8/2016 | Berry et al. |
| 2017/0333492 | A1 * | 11/2017 | Kweon ..................... A61P 3/08 |
| 2019/0083599 | A1 * | 3/2019 | Flavell ................ A61K 39/116 |
| 2019/0328797 | A1 * | 10/2019 | Kweon .................. A23L 33/30 |
| 2019/0336543 | A1 * | 11/2019 | Berry ................. A61K 31/7004 |

FOREIGN PATENT DOCUMENTS

| KR | 1020140082964 A1 | 7/2014 | |
|---|---|---|---|
| WO | 2016033439 A1 | 3/2016 | |
| WO | WO-2016033439 A2 * | 3/2016 | ............. A61P 31/04 |
| WO | 2016093599 A1 | 6/2016 | |

OTHER PUBLICATIONS

Yang et al, Nature, Jan. 2017, 10/1:104-116 (Year: 2017).*
Musso et al, Diabetes Care. Oct. 2010. 33/10:2277-2284. (Year: 2010).*
Honor Health. 2011. Obesity Action Coalition. (Year: 2011).*
Geisinger. Yes, Thin People Can Get Type 2 Diabetes. Nov. 6, 2020. (Year: 2020).*
U.S. Appl. No. 15/534,068, Restriction Election Requirement, dated Apr. 11, 2018, 8 pages.
U.S. Appl. No. 15/534,068, Notice of Allowance, dated Apr. 17, 2019, 6 pages.
U.S. Appl. No. 15/534,068, Non-Final Office Action, dated Sep. 20, 2018, 16 pages.
Berry, et al., "Host-compound foraging by intestinal microbiota revealed by single-cell stable isotope probing", Proc Nati Acad Sci U S A.; 110(12), Mar. 19, 2013, pp. 4720-4725.
Henning, et al., "Health benefit of vegetable/fruit juice-based diet: Role of microbiome", Scientific Reports, 7:2167, May 19, 2017, 9 pages.
Johnson, et al., "Microbiome and metabolic disease: revisiting the bacterial", J. Mol. Med., Review, Nov. 29, 2016, 7 pages.
Miyamoto, et al., "*Bacteroides acidifaciens* sp. nov., isolated from the caecum of mice", International Journal of Systematic and Evolutionary Microbiology, 50, 2000, pp. 145-148.
Petriz, et al., "Exercise induction of gut microbiota modifications in obese, non-obese and hypertensive rats.", BMC Genomics;15:511, 2014, 13 pages.
Walker, et al., "Distinct signatures of host-microbial metametabolome and gut microbiome in two C57BL/6 strains under high-fat diet", The ISME Journal, 8, 2014, pp. 2380-2396.

(Continued)

*Primary Examiner* — Nita M. Minnifield
(74) *Attorney, Agent, or Firm* — Armstrong Teasdale LLP

(57) ABSTRACT

The present disclosure relates to a composition for preventing or treating metabolic diseases, in which the composition includes *Bacteroides acidifaciens* as an active ingredient. In addition, the present disclosure relates to a composition for oxidizing fat or inhibiting DPP-4, in which the composition includes *Bacteroides acidifaciens* as an active ingredient. In addition, the present disclosure relates to a transformant expressing a lean phenotype, in which an Atg7 gene is deleted in dendritic cells.

2 Claims, 24 Drawing Sheets

Specification includes a Sequence Listing.

(56) References Cited

OTHER PUBLICATIONS

White, et al., "Stone Disease: Basic Research & Pathophysiology II Moderated Poster 19", The Journal of Urology, vol. 197, No. 4S, Supplement, May 12, 2017, pp. e229.

Xiong, et al., "Antidiabetic Activity of Ergosterol from Pleurotus Ostreatus in KK-Ay Mice with Spontaneous Type 2 Diabetes Mellitus", Mol. Nutr. Food Res. 62, 2018, 13 pages.

Yanagibashi, et al., "IgA production in the large intestine is modulated by a different mechanism than", Immunobiology 218, 2013, pp. 645-651.

Yang, et al., "Gut commensal Bacteroides acidifaciens prevents obesity and improves insulin sensitivity in mice", Mucosal Immunol. 10(1): doi: 10.1038/mi.2016.42., Jan. 10, 2017, pp. 104-116.

* cited by examiner

[FIG. 1A]
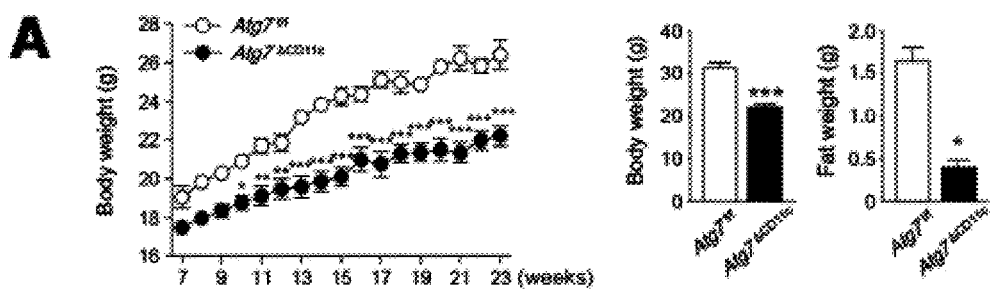
[FIG. 1B]
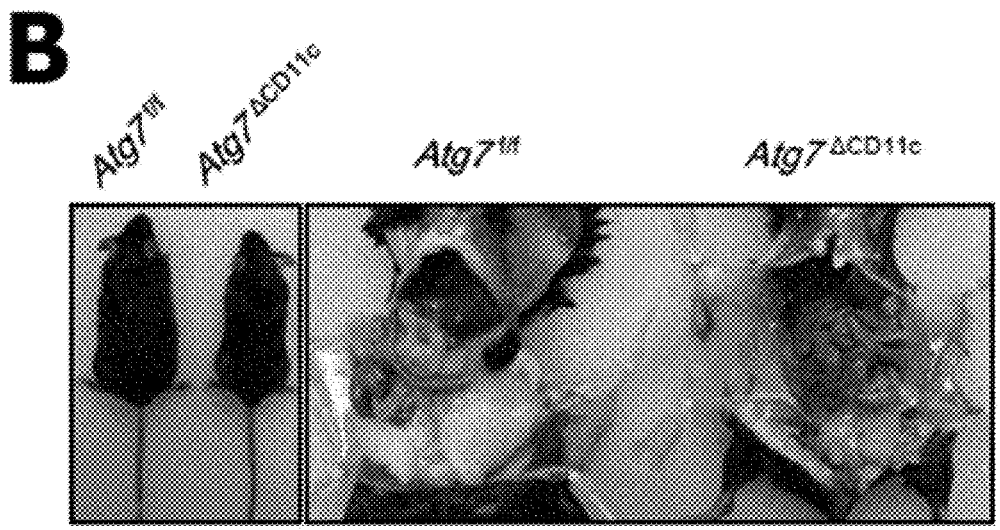
[FIG. 1C]
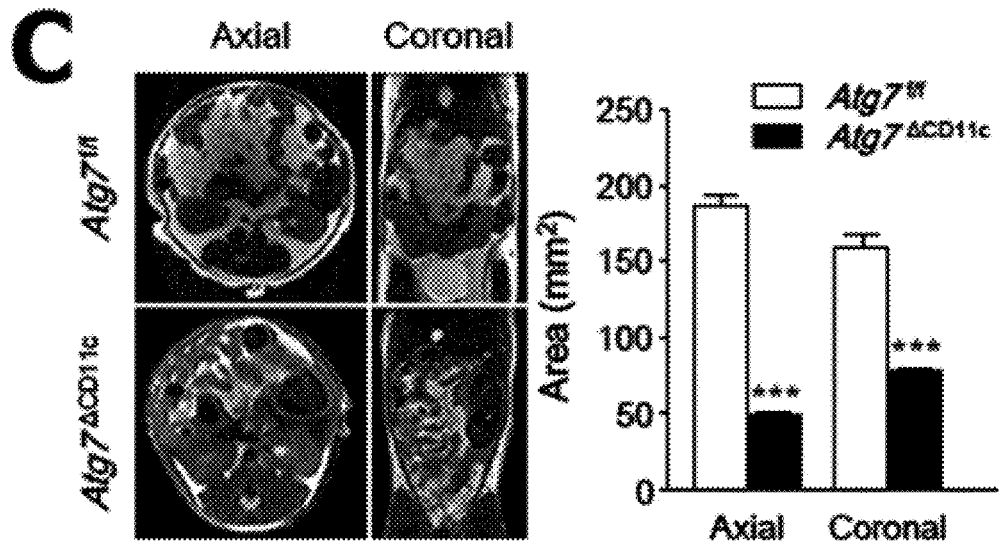

[FIG. 1D]
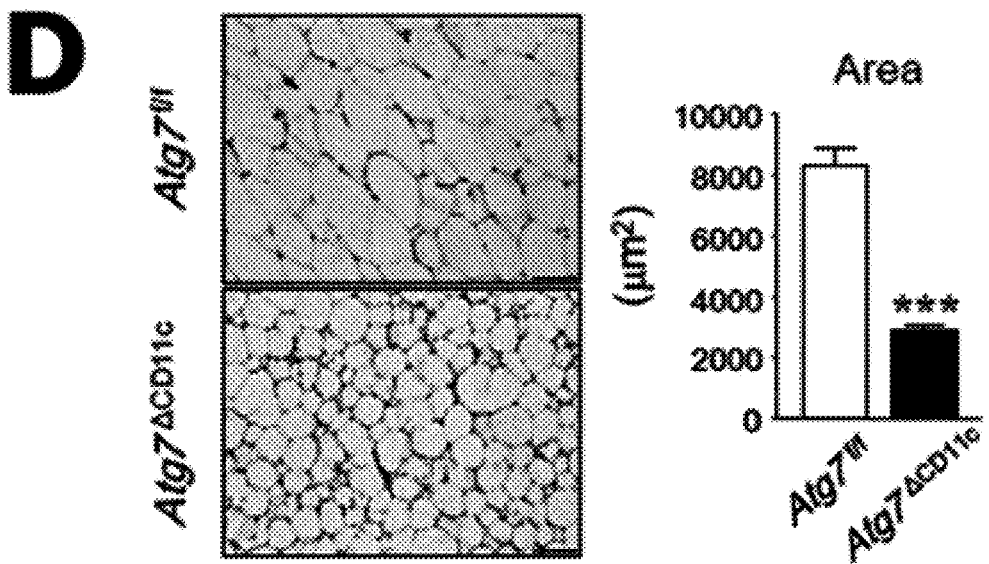
[FIG. 1E]
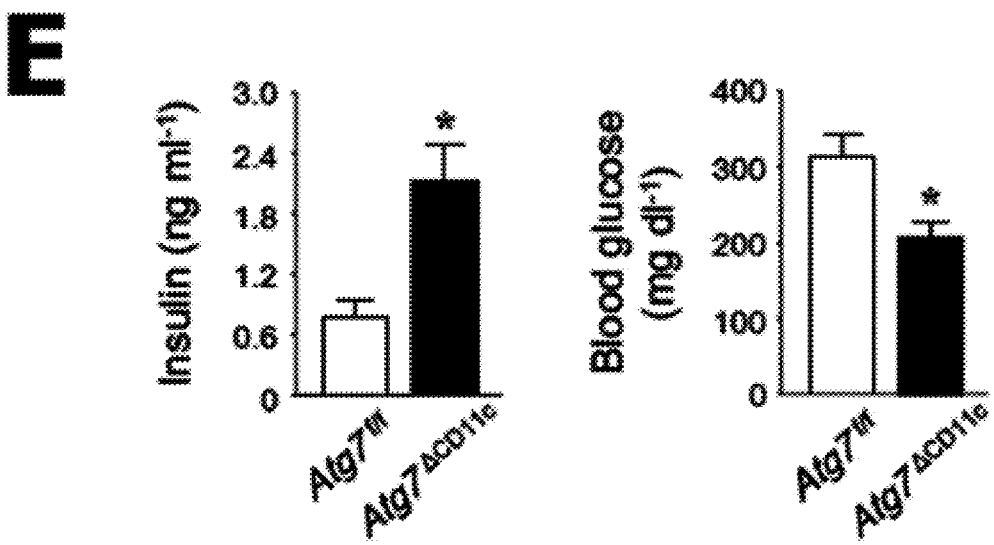
[FIG. 1F]
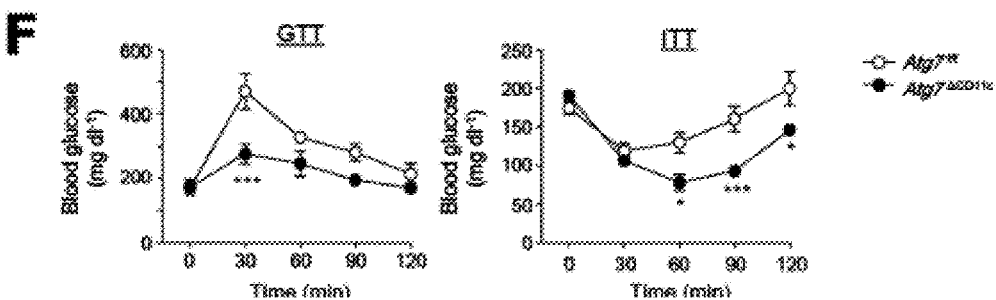

[FIG. 2A]
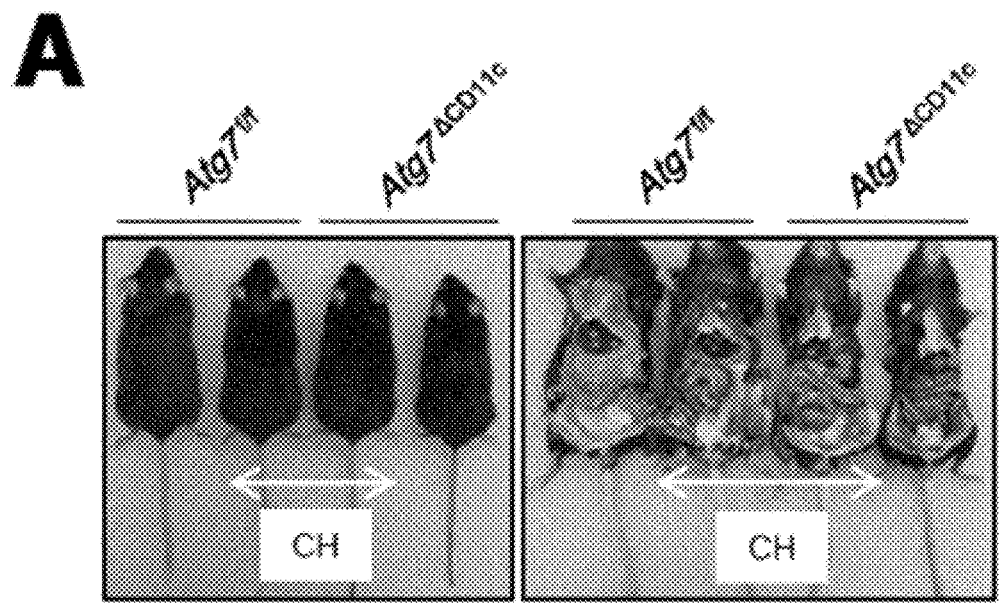
[FIG. 2B]
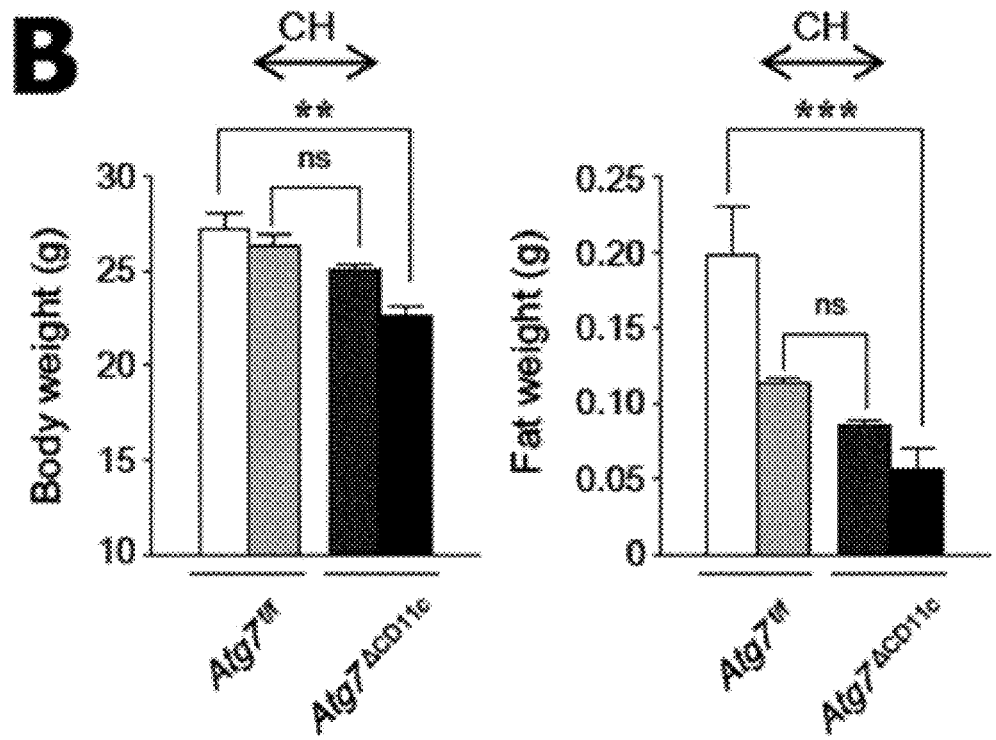

[FIG. 2C]
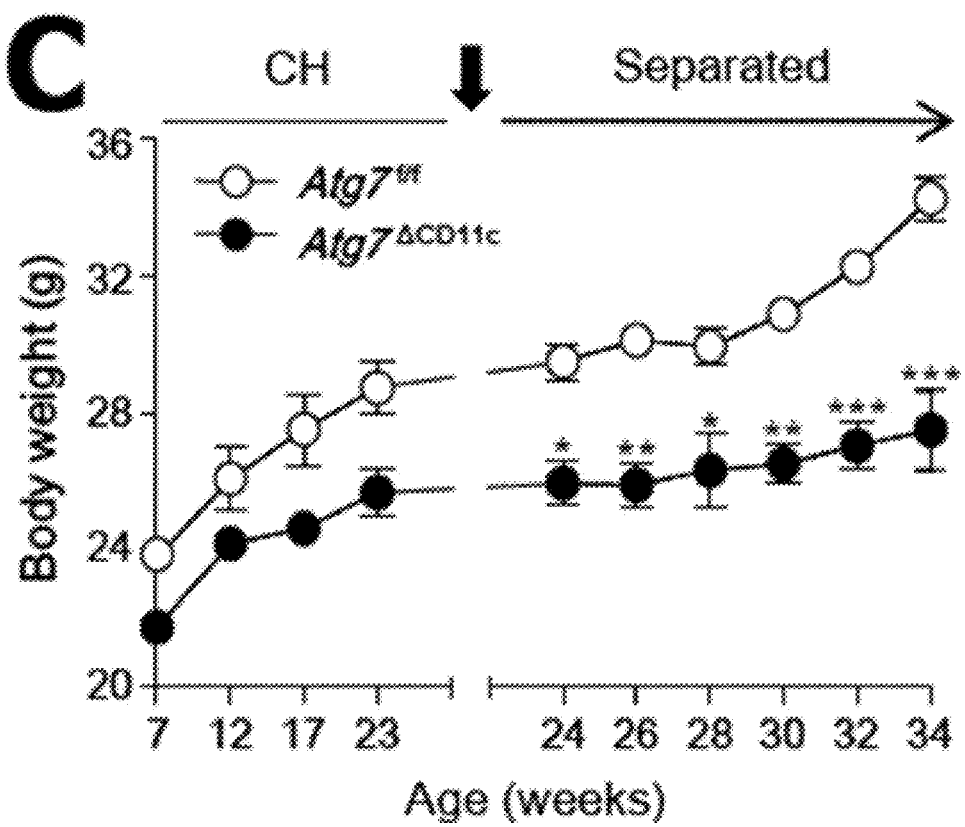
[FIG. 2D]
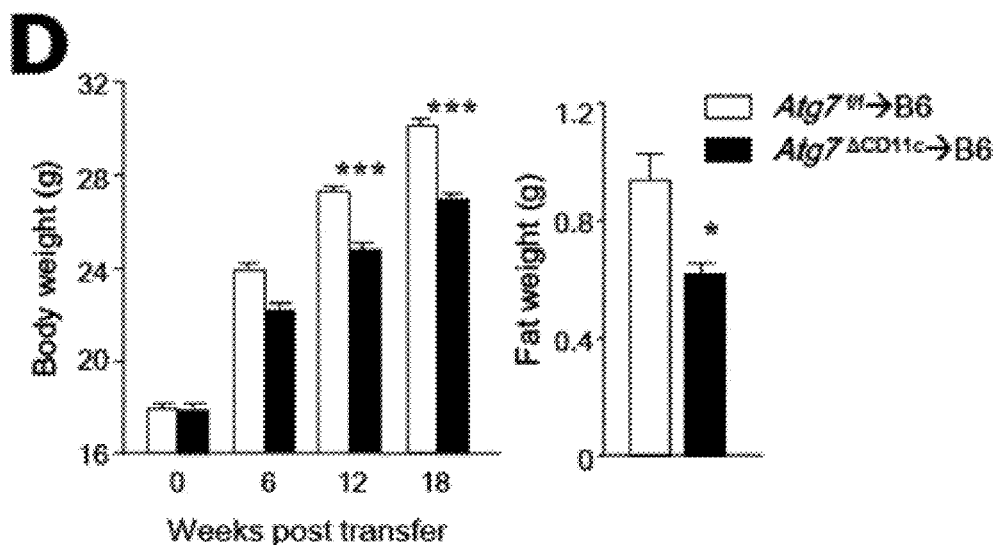

[FIG. 2E]
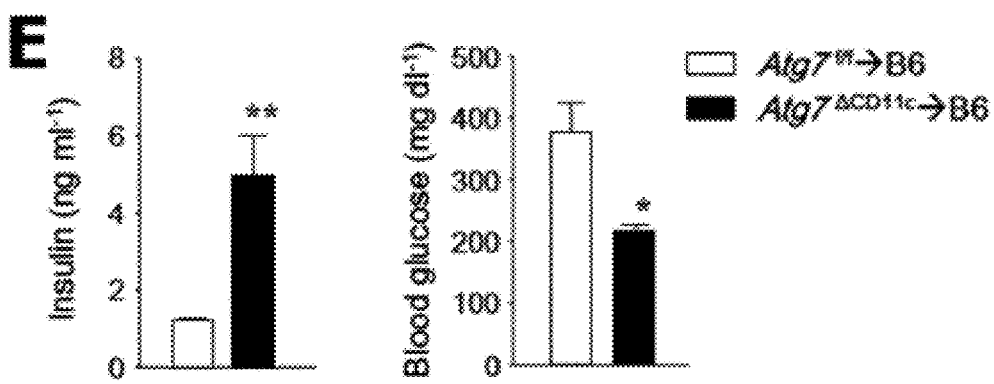
[FIG. 3A]
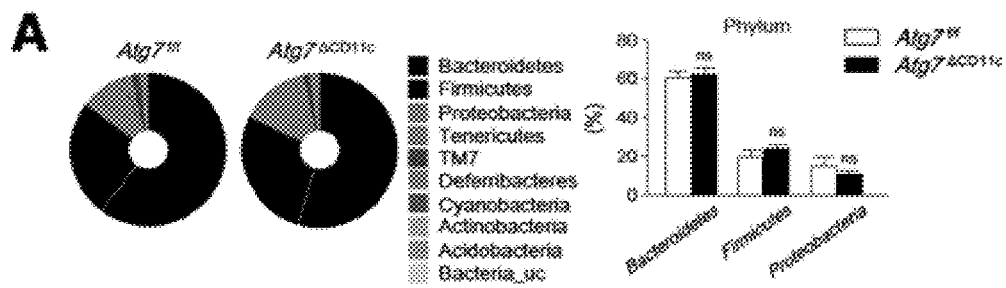
[FIG. 3B]
[FIG. 3C]
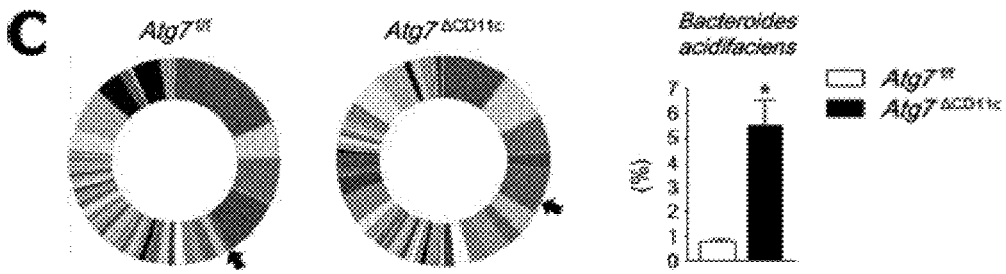

[FIG. 3D]
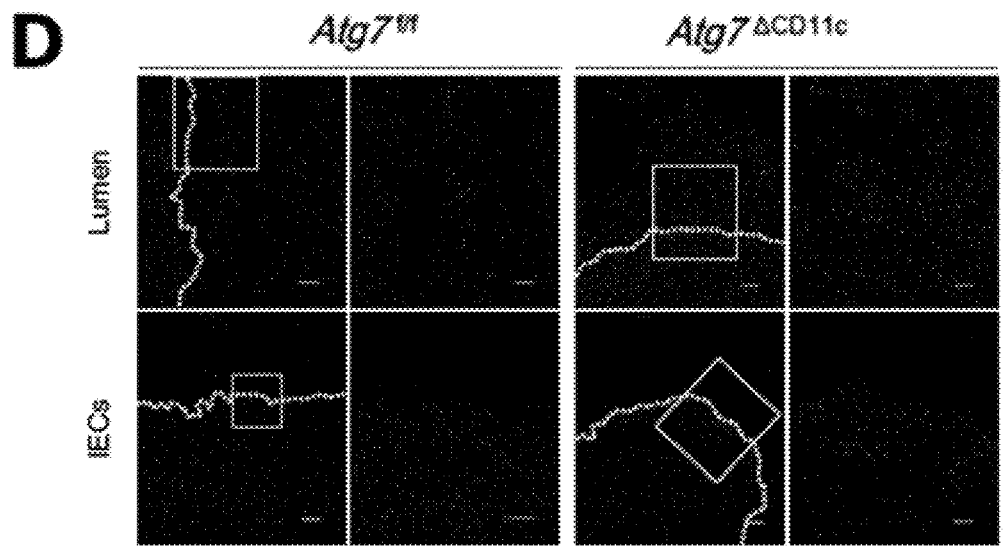
[FIG. 4A]
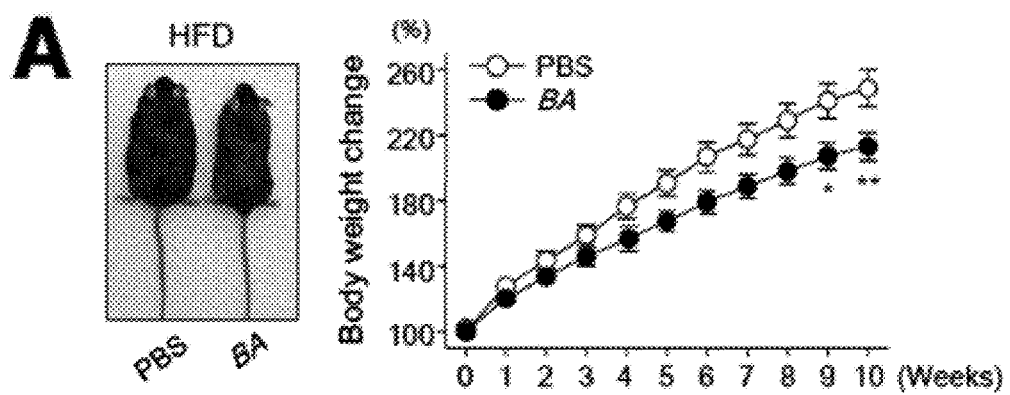

[FIG. 4B]
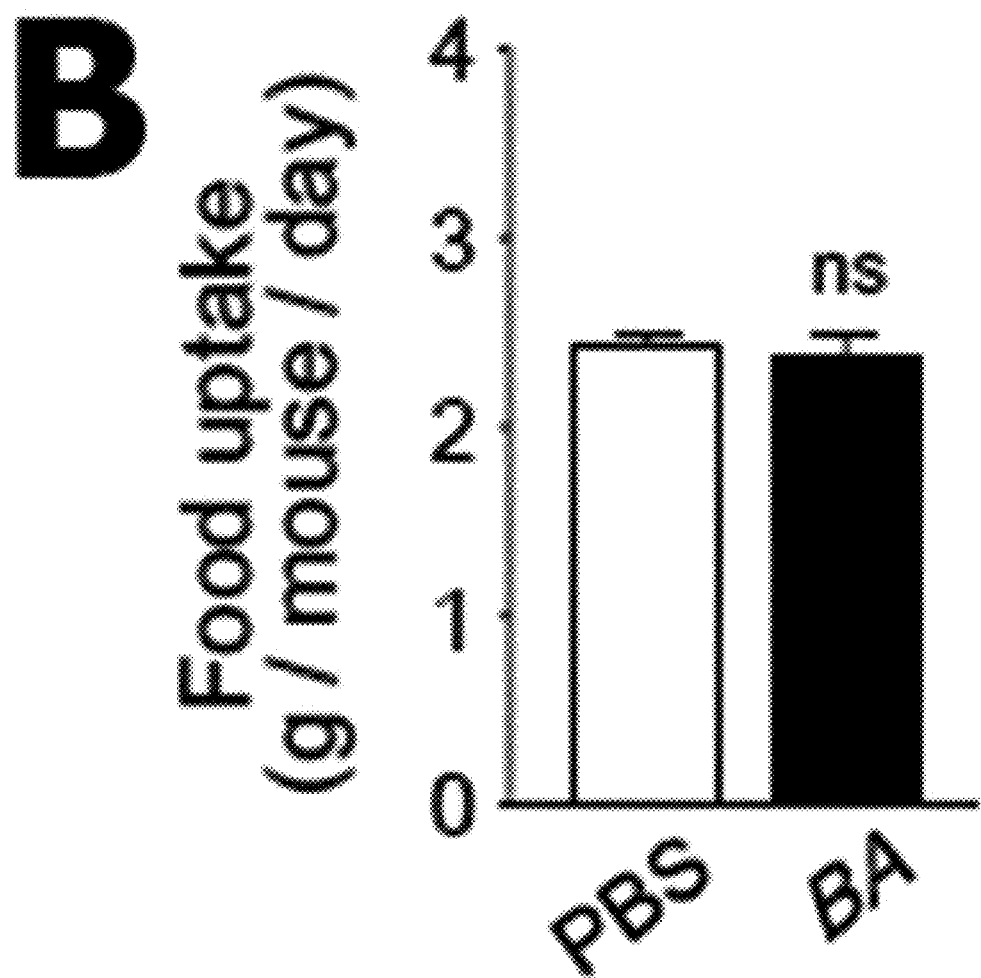

[FIG. 4C]
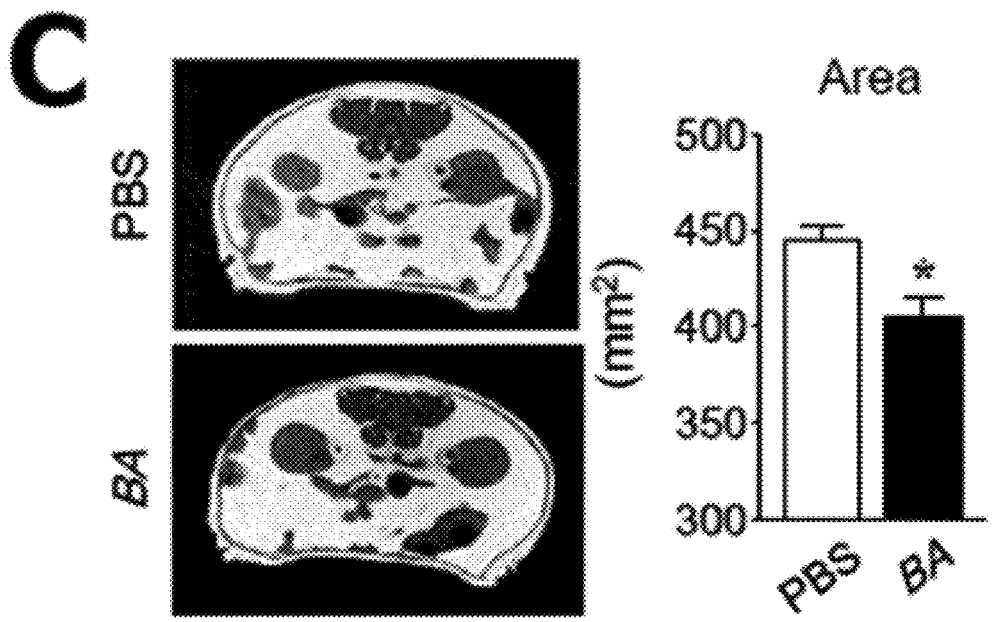
[FIG. 4D]
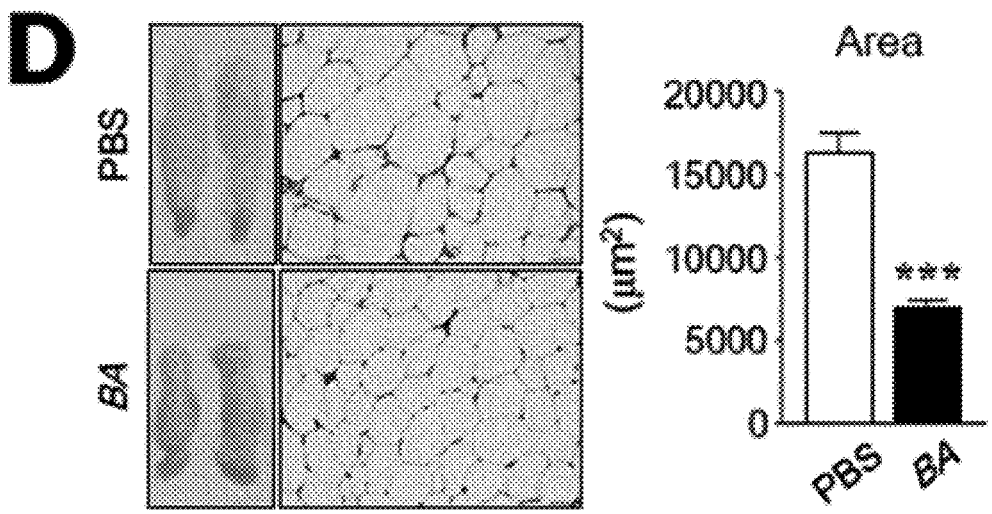

[FIG. 4E]
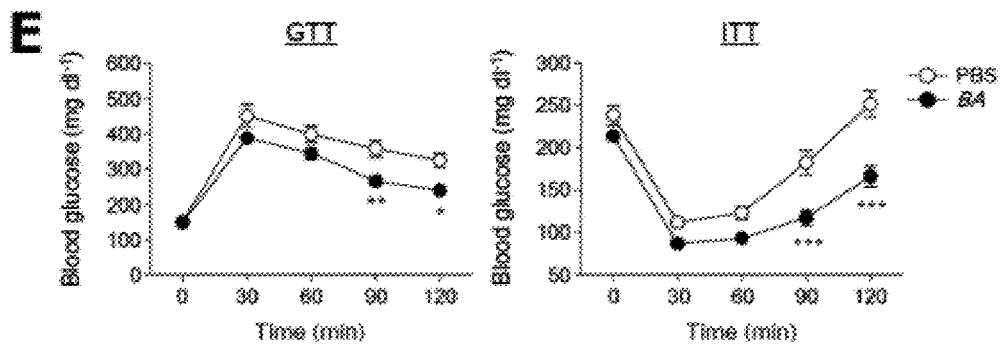
[FIG. 4F]
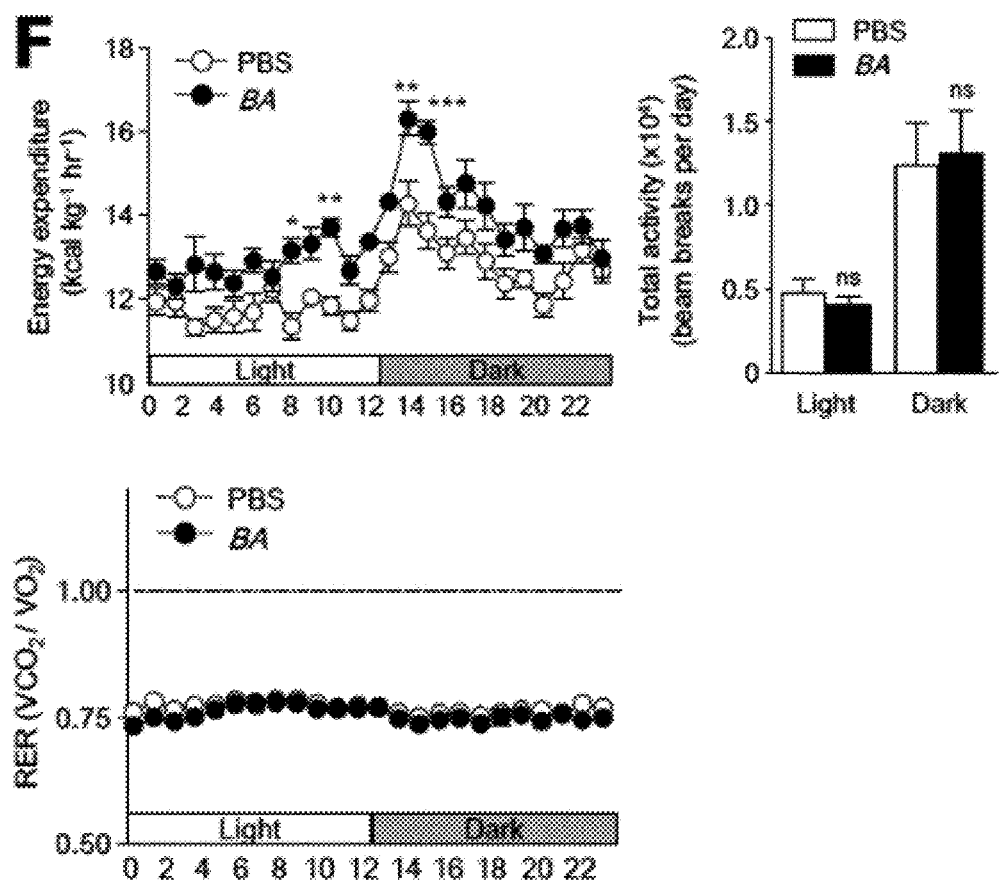

[FIG. 5A]
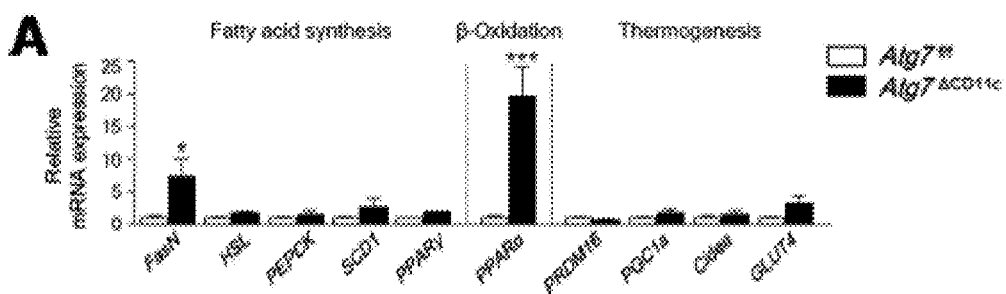
[FIG. 5B]
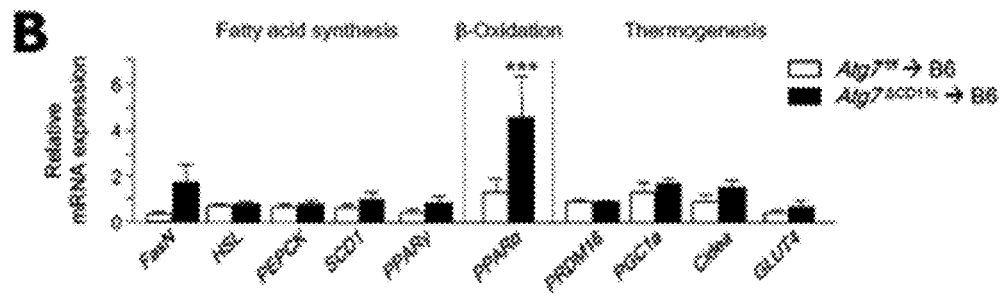
[FIG. 5C]
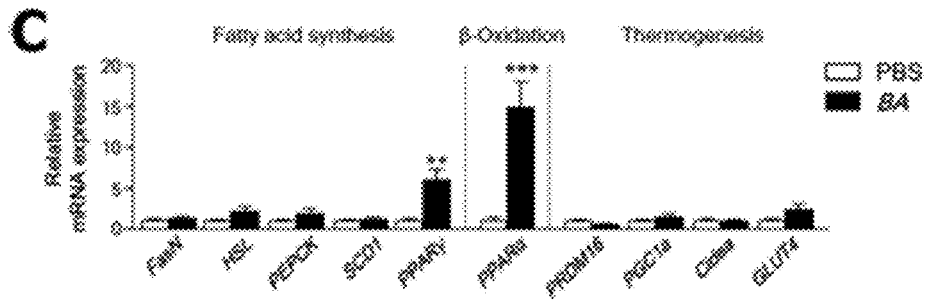
[FIG. 5D]
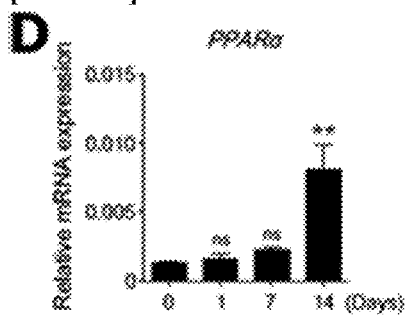
[FIG. 5E]
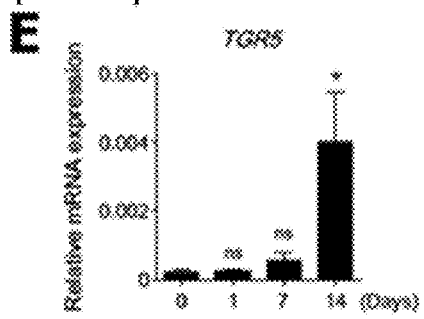

[FIG. 6A]
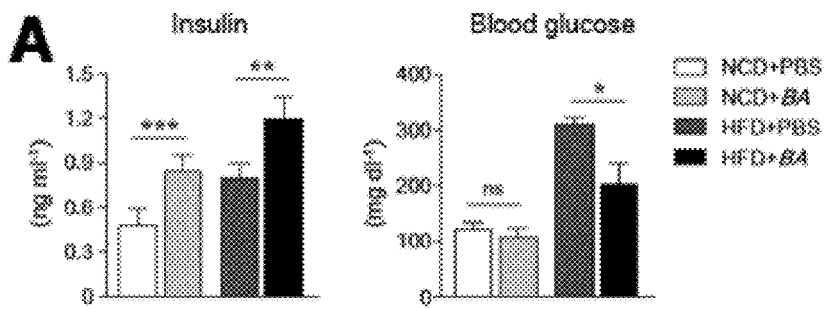
[FIG. 6B]
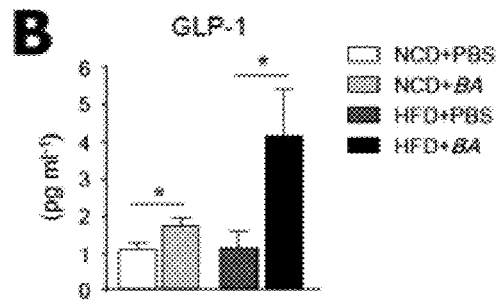
[FIG. 6C]
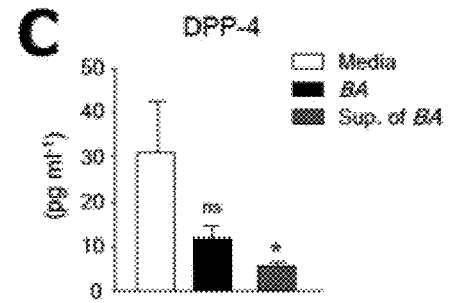
[FIG. 6D]
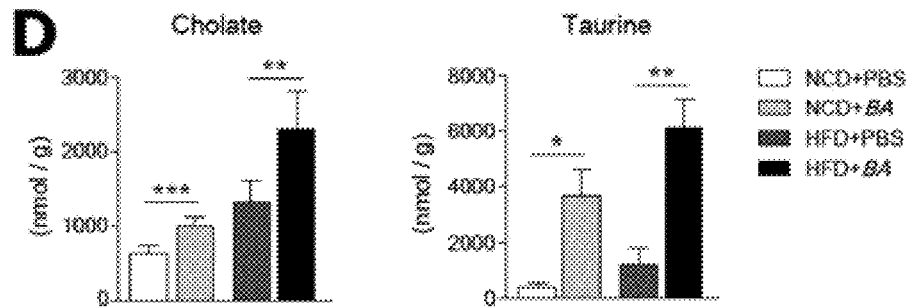

[FIG. 7]
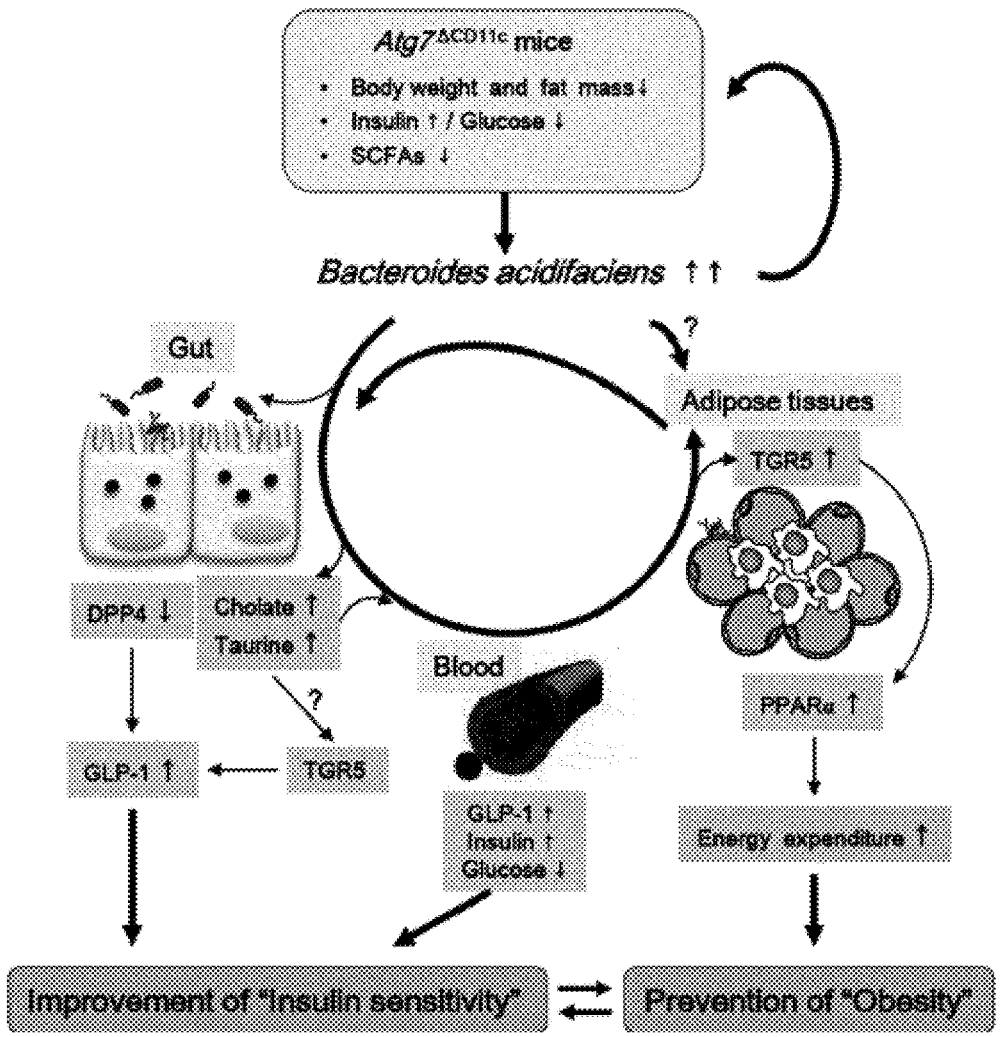
[FIG. 8]
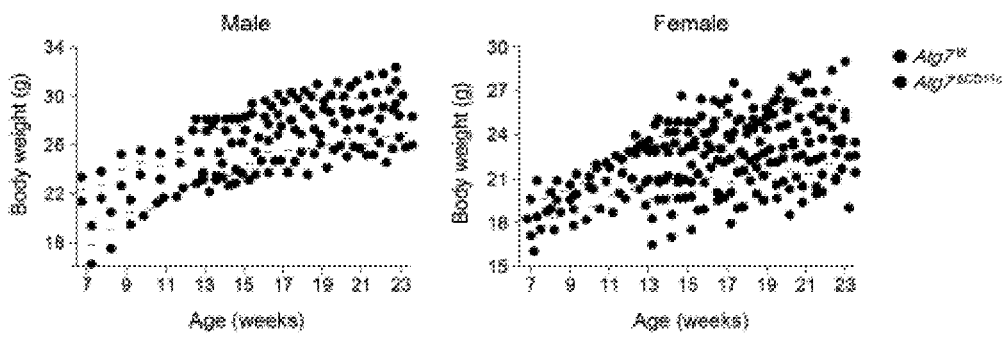

[FIG. 9A]
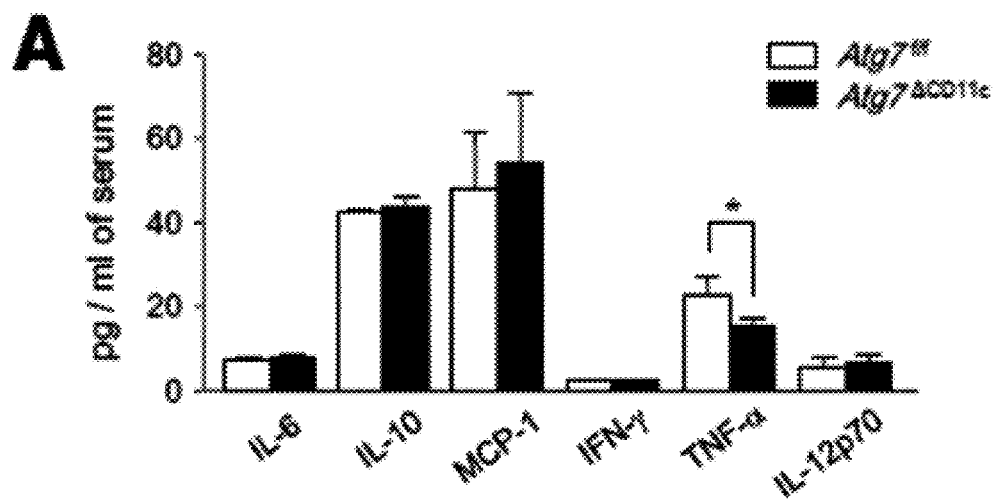
[FIG. 9B]
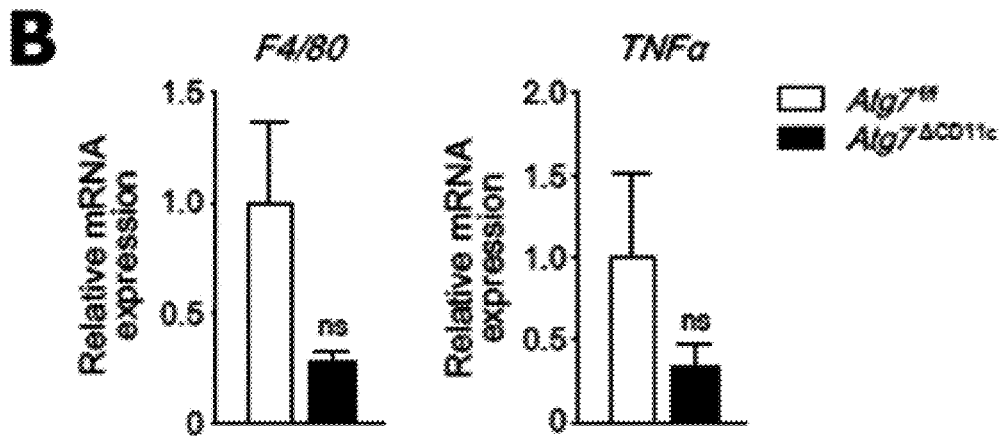

[FIG. 9C]
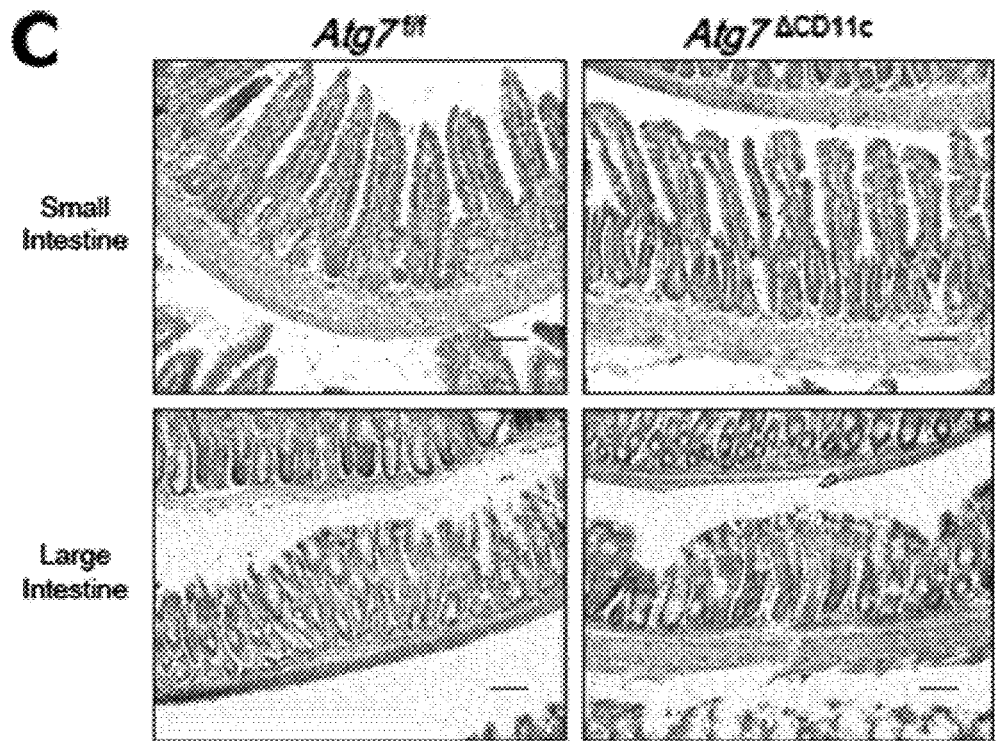
[FIG. 10A]
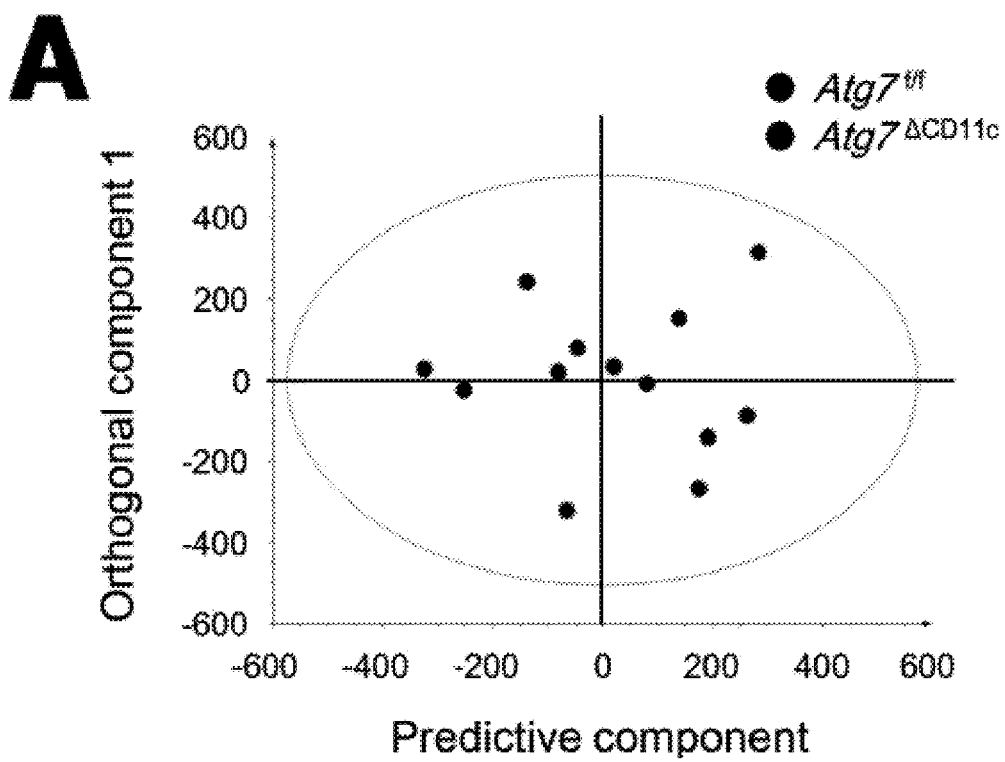

[FIG.10B]
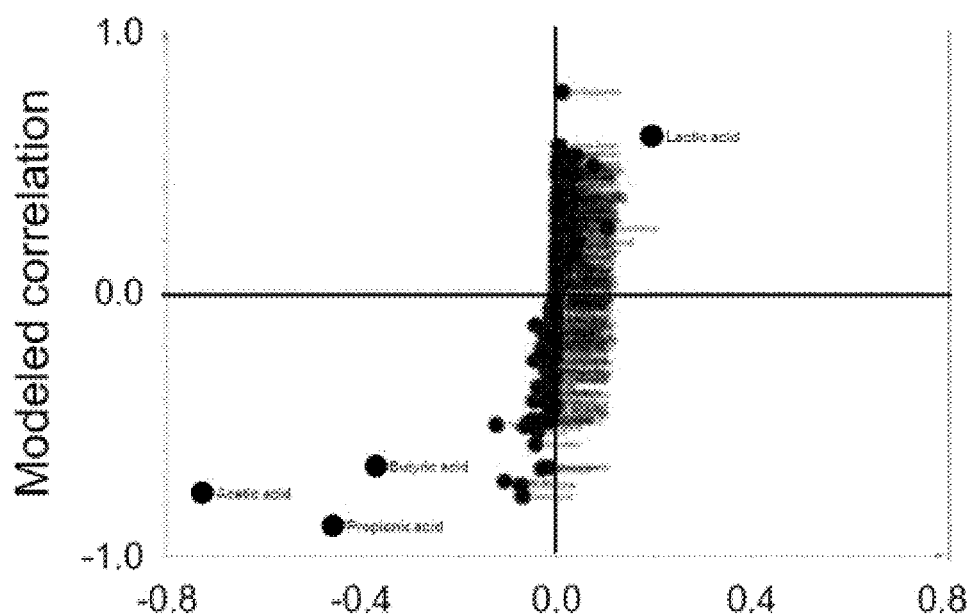
[FIG. 10C]
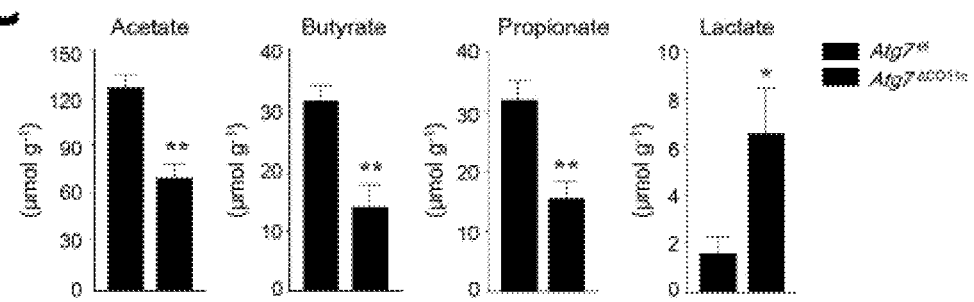

[FIG. 11]
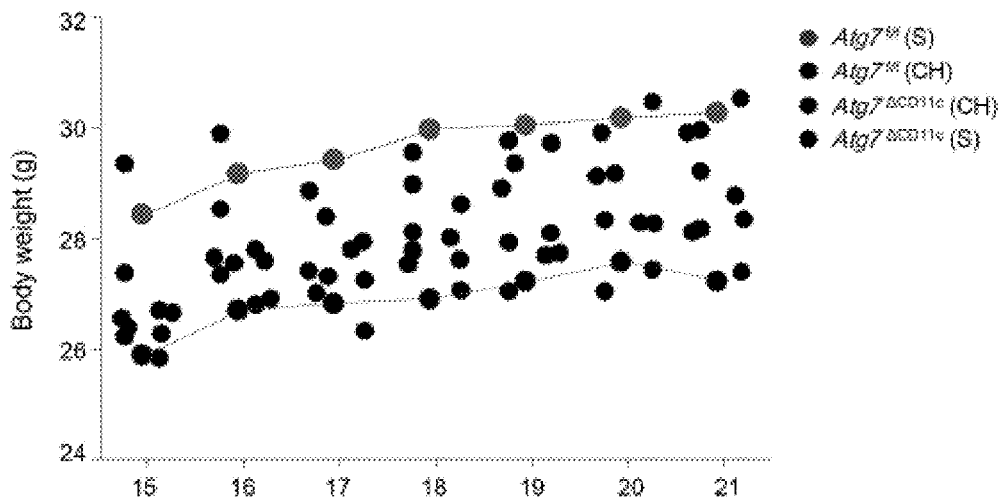
[FIG. 12]
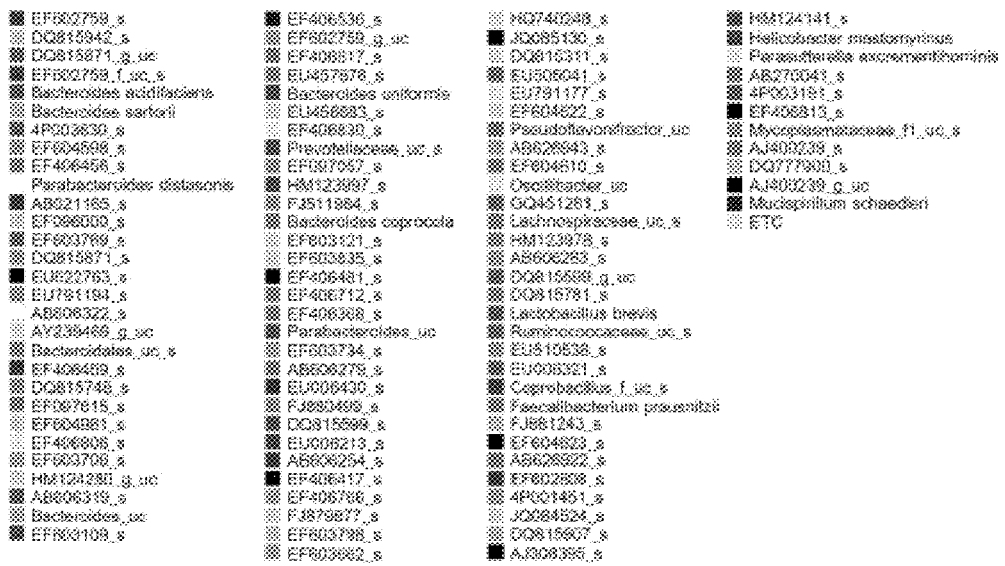

[FIG. 13]
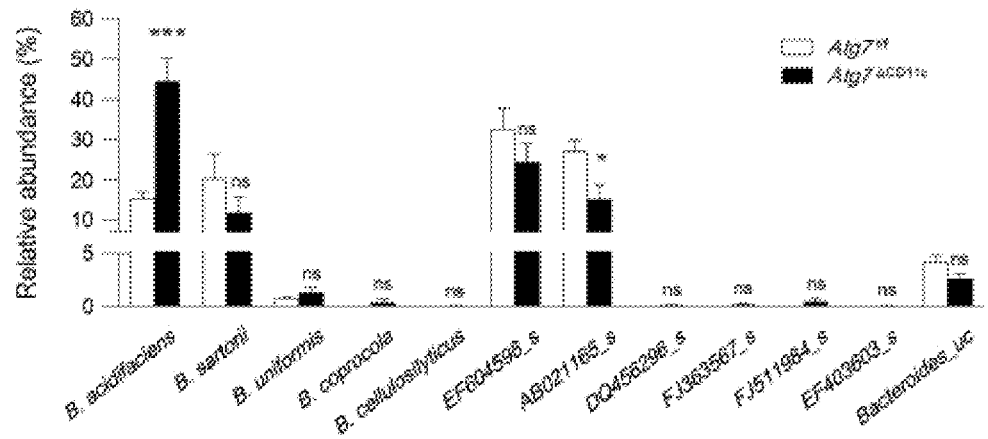
[FIG. 14A]
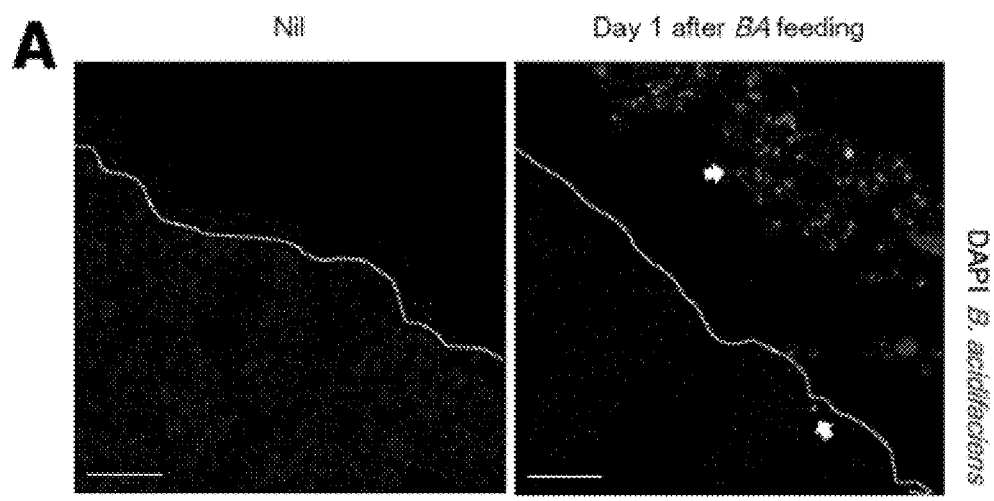
[FIG. 14B]
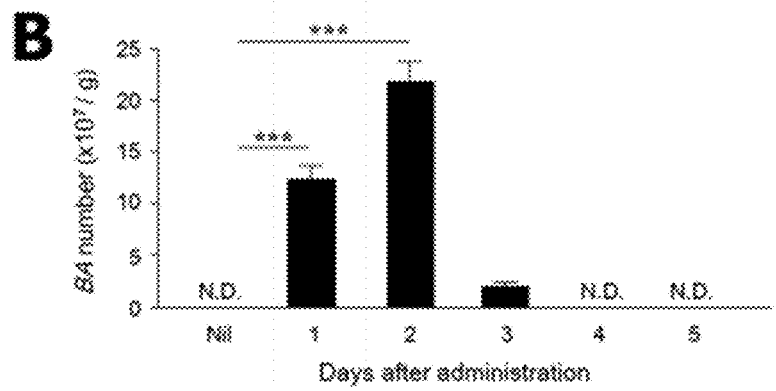

[FIG. 15A]
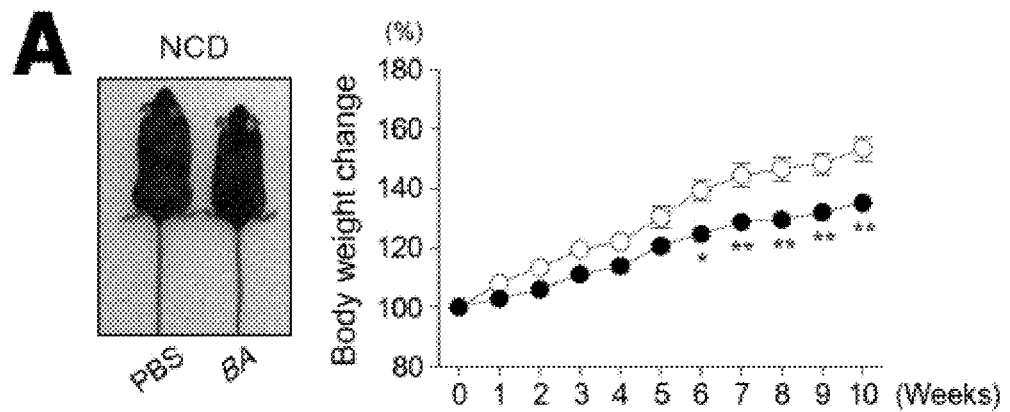
[FIG. 15B]
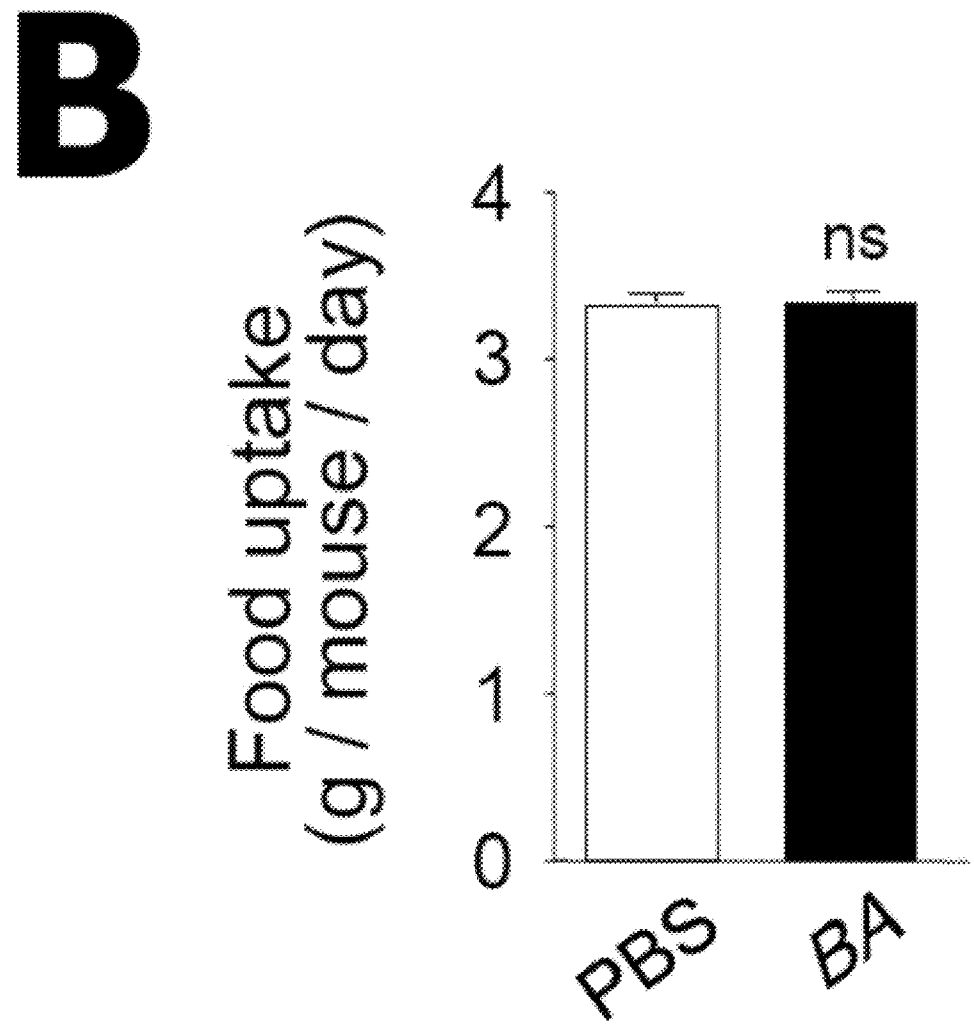

[FIG. 15C]
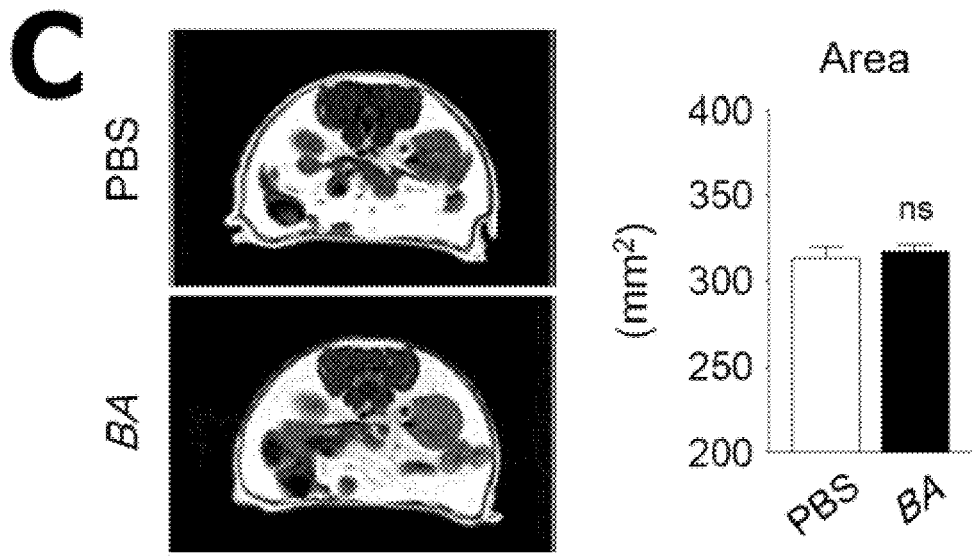
[FIG. 15D]
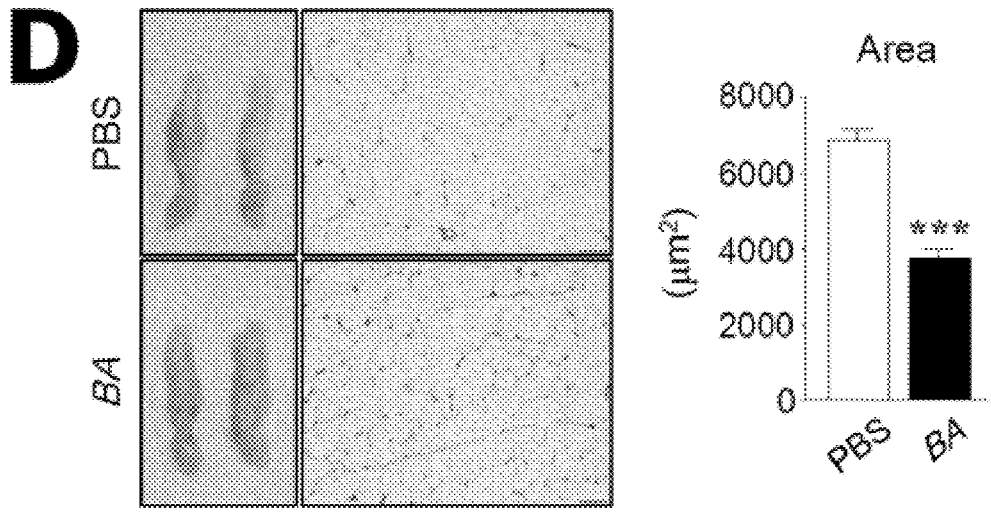

[FIG. 15E]
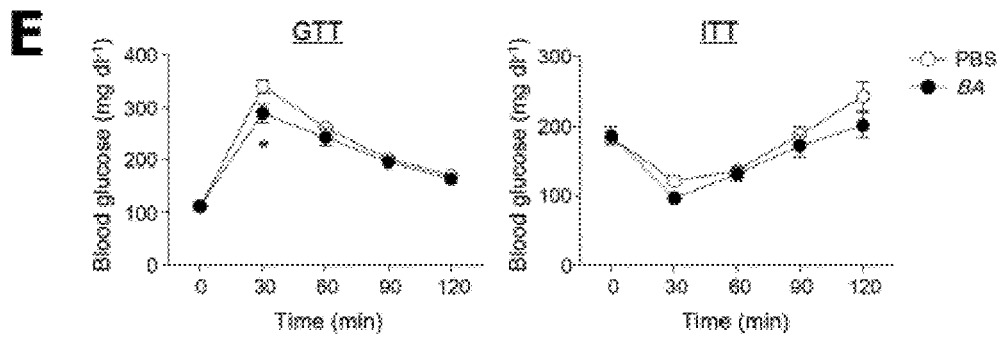
[FIG. 15F]
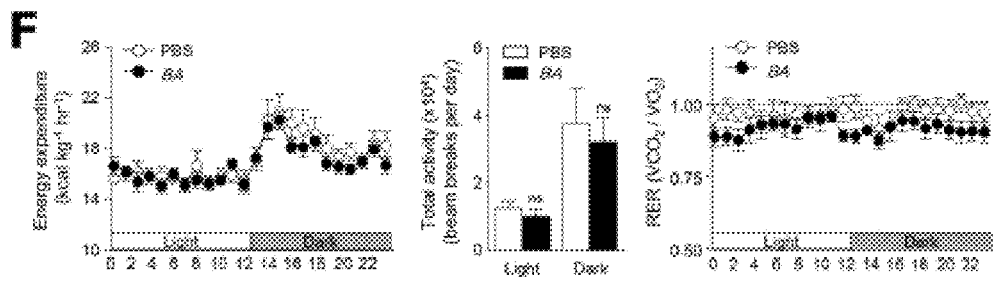
[FIG. 16A]
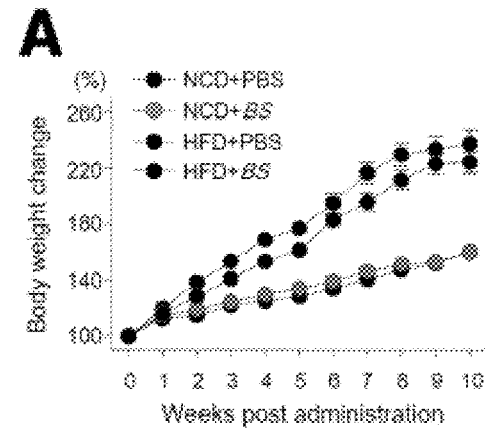
[FIG. 16B]
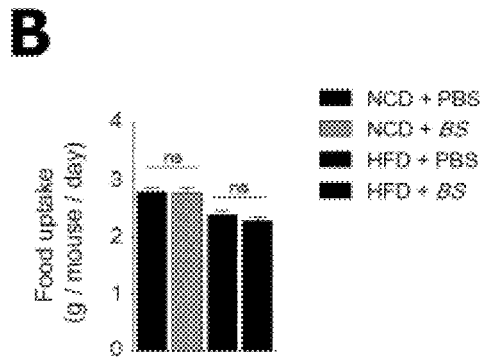

[FIG. 17]
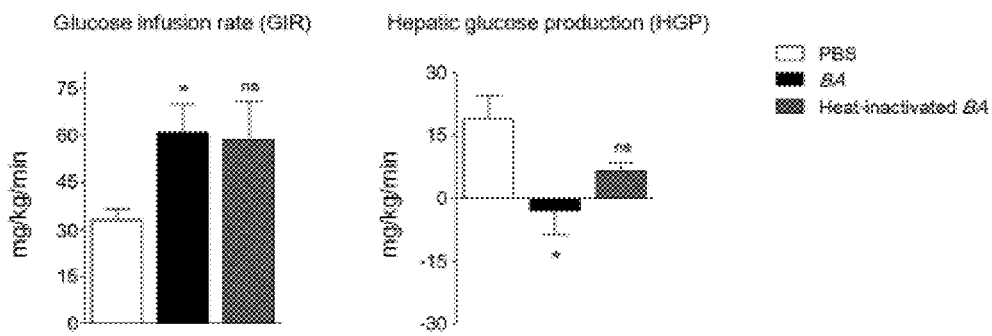
[FIG. 18A]
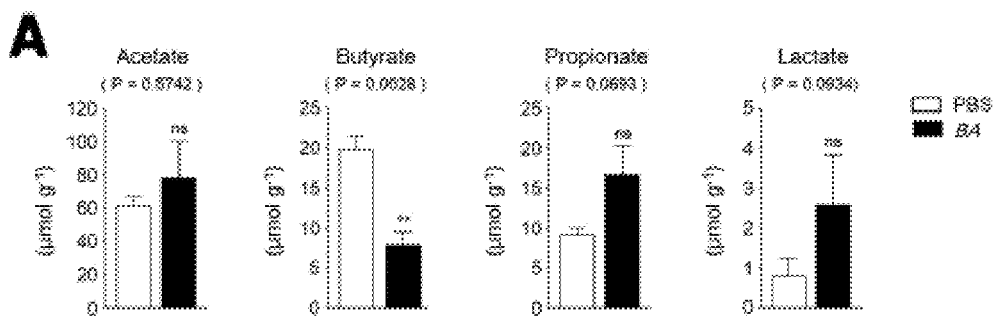
[FIG. 18B]
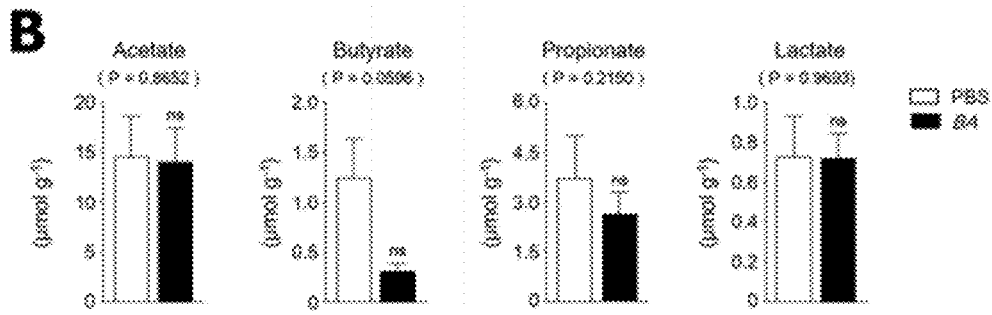

[FIG. 19A]
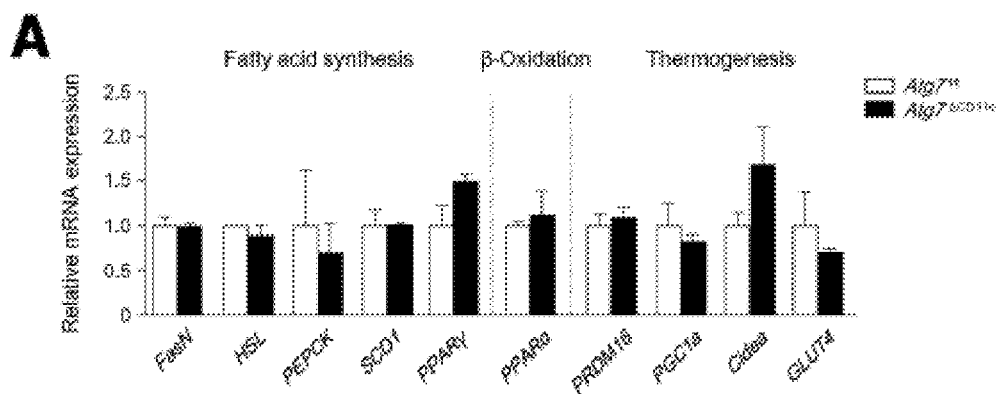
[FIG. 19B]
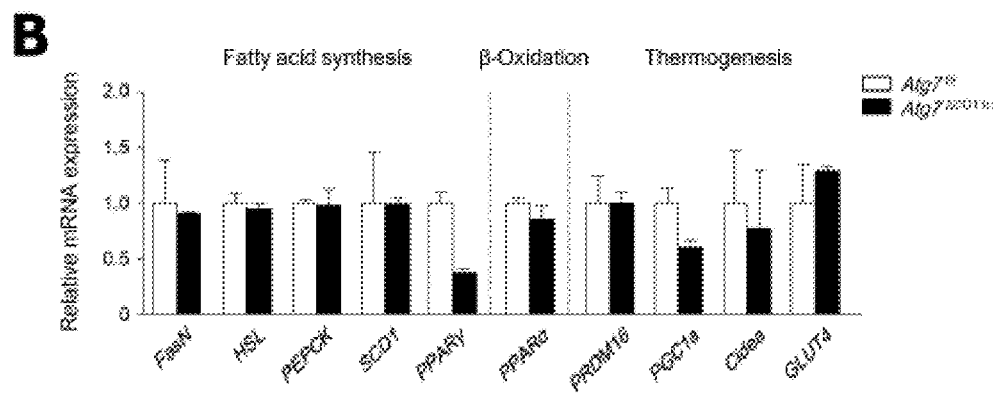
[FIG. 20A]
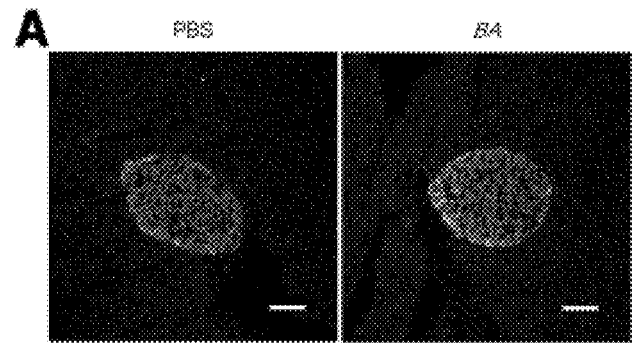
[FIG. 20B]
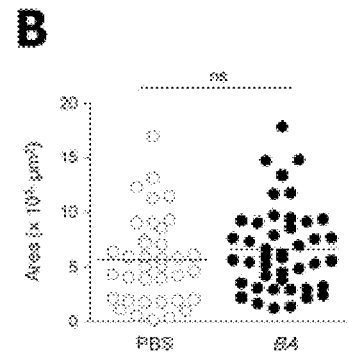

[FIG. 21A]
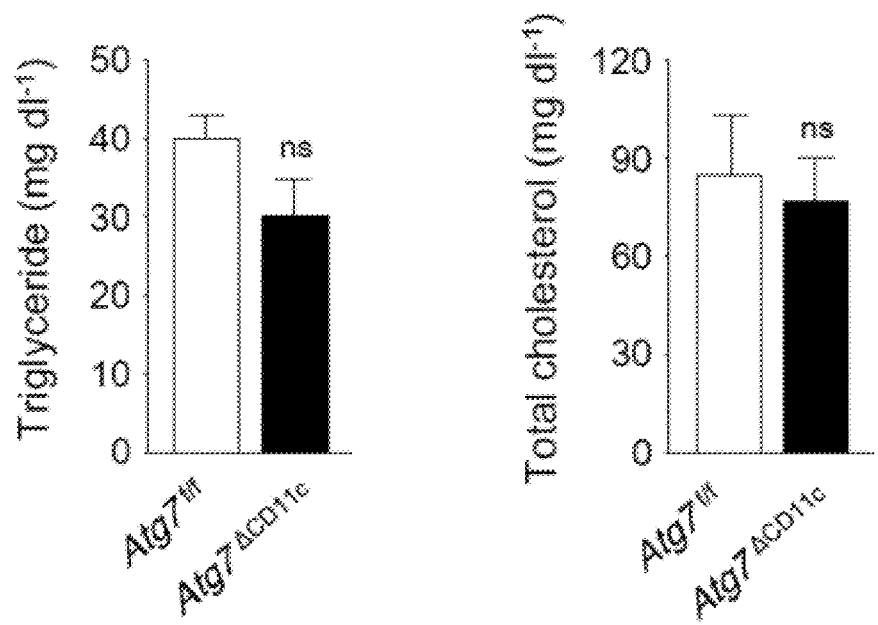
[FIG. 21B]
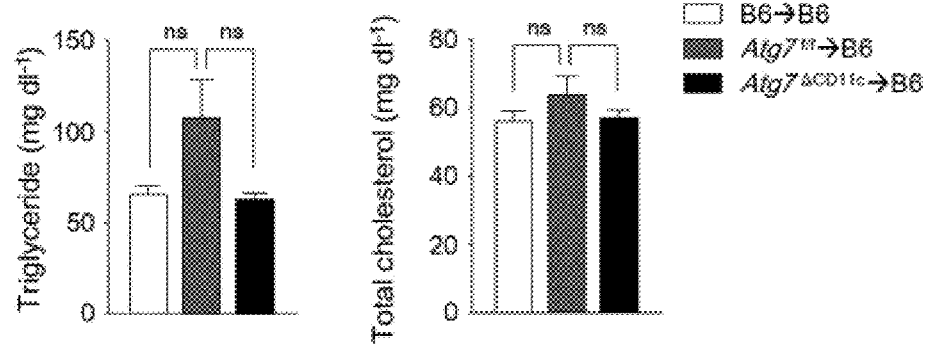

[FIG. 21C]
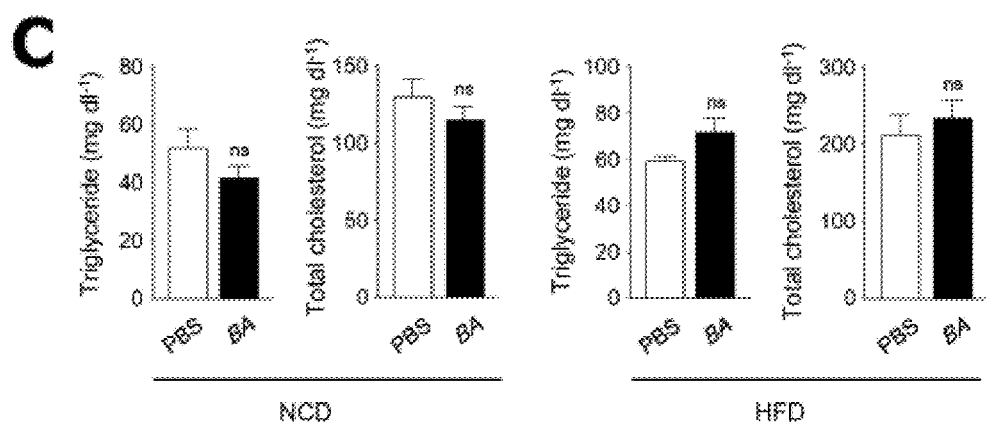
[FIG. 22]
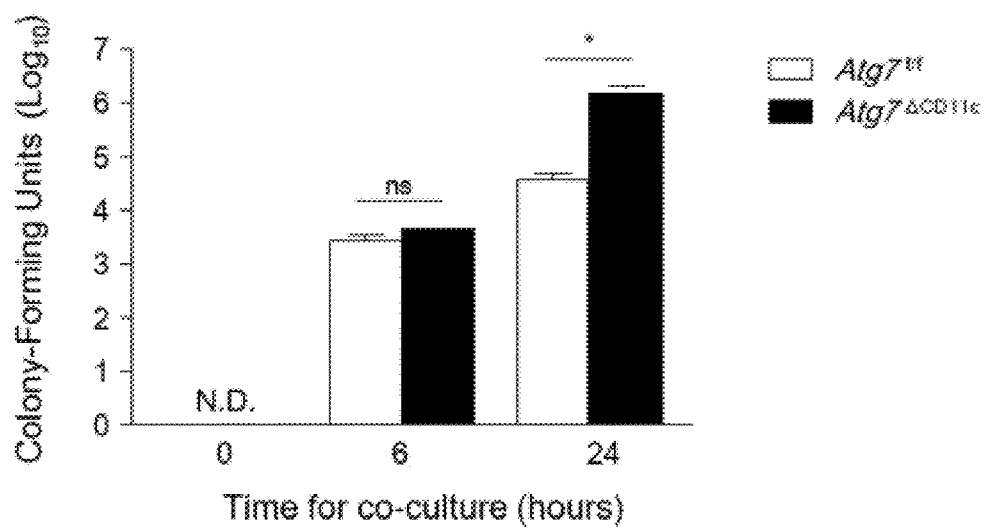

PHARMACEUTICAL COMPOSITION FOR PREVENTING OR TREATING METABOLIC DISEASES, COMPRISING BACTEROIDES ACIDIFACIENS AS ACTIVE INGREDIENT

RELATED APPLICATIONS

This application is a continuation of U.S. patent application Ser. No. 15/534,068, filed Jun. 8, 2017, which is United States National Phase entry of International Application No. PCT/KR2015/013402 filed Dec. 8, 2015, which claims the benefit of Korean Patent Application No. 10-2014-0175349 filed Dec. 8, 2014. The entire contents of each of the foregoing applications is hereby incorporated by reference herein.

TECHNICAL FIELD

The present disclosure relates to a composition for preventing or treating metabolic diseases, in which the composition includes *Bacteroides acidifaciens* as an active ingredient.

In addition, the present disclosure also relates to a composition for oxidizing fat or inhibiting DPP-4, in which the composition includes *Bacteroides acidifaciens* as an active ingredient.

BACKGROUND ART

A metabolic disease is a syndrome that appears with the risk factors such as obesity, diabetes, hypertension and arteriosclerosis caused by excessive nutrition accumulation in the body and lack of exercise. In recent years, it has been formally named the metabolic syndrome or insulin resistance syndrome through the Adult Treatment Program Panel III established by the World Health Organization and the National Heart, Lung, and Blood Institute of the National Institutes of Health. In addition, according to the ATP of the USA National Cholesterol Education Program (NCEP) announced in 2001, it is judged to be a metabolic disease if a patient showing at least three of the five risk factors of abdominal obesity with a waist circumference of 40 inches (102 cm) or longer for men and 35 inches (88 cm) or longer for women, triglycerides of 150 mg/DL or higher, HDL cholesterol of 40 mg/dL or less for men and 50 mg/dL or less for women, blood pressure of 130/85 mmHg or higher, and fasting glucose of 110 mg/dL or higher. In case of Asians, it has been somewhat adjusted that the waist circumference of 90 cm or longer for men and 80 cm or longer for women is considered as abdominal obesity. When these rules are applied, there is a recent study showing that approximately 25% of Koreans among the entire population shows metabolic syndrome symptoms.

On the other hand, mucosal immune tissues refer to tissues covered with mucous membranes ranging from respiratory organs, genital organs and digestive organs, and these tissues are directly connected to the external environment and are easily exposed to foreign antigens and pathogens. In the mucosal tissues of a human body, various microorganisms of nearly 100 trillion such as bacteria, fungi, protozoa, etc. produce clustering, and coexist with them.

In comparison of systemic immune tissues, mucosal immune tissues have an immunological tolerance mechanism to coexist with various symbiotic microorganisms, and at the same time, it has a system that can cause rapid and powerful immune response for the primary defense against pathogenic microorganisms.

Intestinal microorganisms are known to affect human health and diseases by participating in the maintenance of intestinal homeostasis and metabolic regulation through many mechanisms. Intestinal microorganisms ferment undigested polysaccharides to prepare short chain fatty acids and supply the energy source of intestinal epithelial cells. Intestinal microflora of a human being may be broadly divided into four phyla of gram-negative bacteria, Bacteroidetes and Proteobacteira, and gram-positive bacteria, Firmicutes and Actinobacteria.

In particular, obesity is one of the health risk factors associated with diseases such as cardiovascular disease, diabetes and osteoporosis. Recently, many research results have been published showing that obesity is deeply related to changes and diversity of intestinal microflora. In comparison of the intestinal microorganisms of an obese mouse (ob/ob mouse) with those of a normal body weight mouse, it is known that Firmicutes phylum is increased and *Bacteroides* phylum is decreased. Similarly, it has been reported that when low-carbohydrate or low-fat meals are served to obese humans, Bacteroidetes phylum is increased, and in a study of twins, the diversity is decreased and Bacteroidetes phylum is decreased on analysis of intestinal microorganisms of obese humans.

As a result of analyzing intestinal microorganism genetic makeups in lean and obese humans, it was confirmed that there are significant differences in the type and amount of intestinal microbial species. In other words, the result has been reported that obese patients who do not have abundant intestinal microorganisms show symptoms such as adiposity, insulin resistance, dyslipidemia, and inflammatory reaction, and gain body weight more easily than obese humans with abundant intestinal microorganisms.

The interaction between intestinal microorganisms and hosts play an important role in the pathogenesis of obesity and metabolic syndrome. There is a high possibility of preventing/treating obesity by investigating and isolating/identifying the role of microorganisms that are symbiotic in the intestine and causing changes in these interactions using the concept of probiotics.

However, it has not yet been proven that certain intestinal microorganisms are directly involved in lipid metabolism and can affect body weight and fat mass.

DISCLOSURE

Technical Problem

Accordingly, the present inventors have established a transgenic mouse showing a lean phenotype, specified specifically increased intestinal microorganisms in the mouse, and confirmed that the corresponding microorganisms can be effectively involved in internal metabolism, particularly lipid metabolism, and completed the present disclosure.

Accordingly, one aspect of the present disclosure is to provide a composition for preventing or treating metabolic diseases, in which the composition includes the effective microorganisms.

Another aspect is to provide a method for preventing or treating metabolic diseases, in which the method includes administering the effective microorganisms to a subject in need of prevention or treatment of metabolic diseases. The method may further include, prior to administering, identifying a subject in need of prevention or treatment of metabolic diseases (e.g., identifying whether the subject for administration is suffering from or run a risk of developing a metabolic disease).

Another aspect is to provide a use of the above effective microorganisms to be used for the preparation of a pharmaceutical composition for preventing or treating metabolic diseases, or for preventing or treating metabolic diseases.

In addition, one aspect of the present disclosure relates to a composition for oxidizing fat or inhibiting DPP-4 or a composition for preventing or treating diseases associated therewith, in which the composition includes the above effective microorganisms.

In addition, another aspect of the present disclosure relates to a method for inhibiting DPP-4 or promoting fat oxidation or a method for preventing or treating diseases associated therewith, in which the method includes administering the effective microorganisms to a subject in need of DPP-4 inhibition. The method may further include, prior to administering, identifying a subject in need of DPP-4 inhibition or fat oxidization, or a subject in need of prevention or treatment of the diseases associated therewith.

Another aspect relates to a use of the above effective microorganisms to be used for the DPP-4 inhibition or fat oxidization or for preventing or treating the diseases associated therewith, or a use of the above effective microorganisms to be used for the preparation of a pharmaceutical composition for inhibiting DPP-4 or oxidizing fat or for preventing or treating the diseases associated therewith.

Another aspect of the present disclosure relates to a transformant expressing a lean phenotype, in which an Atg7 gene is deleted in dendritic cells.

Another aspect relates to a method for preparing a transformant exhibiting a lean phenotype, in which the method includes deleting an Atg7 gene in dendritic cells.

In addition, another aspect of the present disclosure relates to a pharmaceutical composition for preventing or treating metabolic diseases, in which the pharmaceutical composition includes Atg7, and an expression inhibitor or an activity inhibitor of a gene coding the same as active ingredients.

Technical Solution

One aspect of the present disclosure provides a pharmaceutical composition for preventing or treating metabolic diseases, in which the pharmaceutical composition includes *Bacteroides acidifaciens* as an active ingredient. Another aspect provides a method for preventing or treating metabolic diseases, in which the method includes administering *Bacteroides acidifaciens* to a subject in need of prevention or treatment of metabolic diseases. The method may further include, prior to administering, identifying a subject in need of prevention or treatment of metabolic diseases. Another aspect is to provide a use of *Bacteroides acidifaciens* to be used for the preparation of a pharmaceutical composition for preventing or treating metabolic diseases or for preventing or treating metabolic diseases.

Hereinafter, the present disclosure will be described in detail.

In a specific example, the present inventors confirmed that when an Atg7 gene was deleted in dendritic cells, a lean phenotype was expressed in the mouse, and then the intestinal microorganisms were compared with a control group, and confirmed that *Bacteroides acidifaciens* was present at a high level in an Atg7$^{\Delta CD11c}$ mouse expressing a lean phenotype. In addition, it has been confirmed that *Bacteroides acidifaciens* reduces the body weight and body fat of a mouse, reduces blood glucose levels, and increases blood insulin production.

In addition, *Bacteroides acidifaciens* (BA) according to the present disclosure causes fat oxidation activity through a bile acid-TGR5-PPARα axis in adipose tissues, resulting in high energy consumption. At the same time, BA activates visceral DPP-4, followed by the increase in GLP-1, thereby contributing to glucose homeostasis. Bile acids, cholate and taurine contributed to GLP-1 activity through a TGR5 receptor and improved insulin sensitivity.

Accordingly, *Bacteroides acidifaciens* of the present disclosure may be used as a pharmaceutical composition for preventing or treating metabolic diseases.

The above *Bacteroides acidifaciens* is a concept including not only microbial cells themselves but also cultures of the bacteria, for example, cultures containing microbial cells or cultures excluding microbial cells, dried materials, fragments, fractions of the cultures, and the like.

The term "metabolic disorder" used in the present specification refers to a disease selected from the group consisting of obesity, diabetes, diabetic complication, fatty liver, hypertension, peripheral vascular disease, dyslipidemia, insulin resistance, cardiovascular disease, arteriosclerosis, metabolic syndrome, hyperglycemia, hyperlipidemia, carbohydrate metabolic abnormality, and the like.

Obesity is an example of the metabolic disease. The term "obesity" in the present disclosure is a disease defined as an increase in the number of adipocytes and an expansion of cell volume, and may be a major cause of metabolic diseases such as diabetes, hypertriglyceridemia, hypertension, cardiovascular disease, blood coagulation defect kidney disease, eye disease, and foot infection, etc.

In addition, as another example of metabolic diseases, "diabetes" is a disease in which insulin is deficient or insulin sensitivity is reduced, resulting in an abnormality in carbohydrate metabolism, and is divided into type 1 diabetes which results from a condition that the pancreas produces little insulin (insulin-dependent diabetes mellitus: IDDS) and type 2 diabetes which begins with a rejection of tissue to insulin (non-insulin-dependent mellitus: NIDDM).

More than 90% of all diabetes is type 2 diabetes. Type 2 diabetes is known to be closed associated with heredity and obesity, especially abdominal obesity (a state that a ratio of waist circumference:a hip circumference is 85:100 or more). Accordingly, in the present disclosure, diabetes preferably means type 2 diabetes. The metabolic diseases may include complications of diabetes. Acute complications of diabetes (hypoglycemia, ketoacidosis or nonketotic hyperosmolar coma) can occur when diabetes is not adequately controlled. Prolonged serious complications include cardiovascular disease (double risk), chronic renal failure, retinal damage that can lead to blindness, many types of nerve damage, and microvascular damage, which cause erectile dysfunction and poor healing. Slow healing of wounds (especially, feet) can cause gangrene, which can lead to amputation.

In the present specification, the term "fatty liver" refers to a phenomenon in which neutral fat, which is not present in normal cells, is shown to be abnormally deposited in liver cells.

In the present specification, hypertension refers to a state in which the blood pressure of arteries is chronically high and an adult over 18 years of age has a systolic blood pressure of 140 mmHg or higher, or a diastolic blood pressure of 90 mmHg or higher, and may be caused by obesity.

The term "peripheral vascular disease (PVD)" refers to damage, dysfunction, and the like of peripheral artery and venous.

The dyslipidemia of the present disclosure means a combination of low high-density lipoprotein cholesterol (HDLc), high triglyceride concentration and slightly high or normal low-density lipoprotein cholesterol (LDLc) concentration.

In addition, the insulin resistance of the present disclosure means a metabolic state in which insulin action, which is the most important biological hormone for controlling total energy metabolism such as carbohydrate, lipid and protein, at a physiological insulin concentration, is declined than normal.

The arteriosclerosis of the present disclosure refers to a state that fatty substances (plaque) containing cholesterol, phospholipid, calcium, etc. are accumulated in the endangium, and arteries become hardened, lose elasticity and become narrow, thereby causing obstruction to blood supply and causing arteriorrhexis, artery dissection, etc. due to high pressure.

The hyperglycemia of the present disclosure refers to a state in which the blood sugar level rises abnormally, and may be due to an abnormality in insulin production or an insulin dysfunction.

The hyperlipidemia of the present disclosure in a condition in which lipid components such as blood cholesterol increase, blood does not flow smoothly, the lipid components are adhered to artery walls, resulting in a chronic inflammatory response, and the narrowing of the wall of an artery causes atherosclerosis that leads to hardening of blood vessels. In the long term, thrombosis produced therefrom causes cardiac infarction, stroke or cerebral infarction, etc. by occluding heart coronary arteries and cerebral blood vessels.

Hyperinsulinemia means a state in which blood insulin levels are higher than normal, and there are organic hyperinsulinemia and functional hyperinsulinemia. The organic hyperinsulinemia is caused by proliferation (adenoma, hypertrophy) of Langerhans islet, resulting in excessive secretion of insulin from the pancreas, and becoming in spontaneous hypoglycemia. Functional hyperinsulinemia is caused by autonomic nervous system and dysfunction of the digestive system without Langerhans soma adenoma. It means that the insulin level of postprandial diet is increased mainly by the cause of stroke and hepatitis after gastrectomy, and hypoglycemia occurs 2 to 4 hours after the meal.

The metabolic disorder of carbohydrate according to the present disclosure is a metabolic disease caused by a problem in the process of glucose biosynthesis for producing glucose from pyruvic acid or a problem in TCA circuit and oxidative phosphorylation process for producing carbon dioxide and water from pyruvic acid. Glycogen storage disease type 1, a fructose-1,6-bisphosphatase deficiency, a pyruvate dehydrogenase complex deficiency, a pyruvate carboxylase deficiency, a glycogenosis, a galactosemia, and the like are the examples thereof, but are not limited thereto.

In addition, as an example of a metabolic disease, there is the metabolic syndrome. The metabolic syndrome is characterized by a group of metabolic risk factors including the following to those skilled in the art: abdominal obesity (excess adipose tissue in and around the abdomen); atherosclerotic dyslipidemia (increased blood fat disease—high triglyceride, low HDL cholesterol and high LDL cholesterol—plaque formation on arterial walls); increased blood pressure; insulin resistance or glucose hypersensitivity; a prothrombotic state (e.g., high fibrinogen or PAI-1 (plasminogen activator inhibitor-1) in the blood); and a pro-inflammatory state (e.g., an increase in C-reactive protein in the blood). People suffering from metabolic syndrome are at increased risk for coronary heart disease and other diseases associated with plaque buildups on arterial walls (such as stroke and peripheral vascular disease), and type 2 diabetes.

Another example of metabolic diseases includes cardiovascular or cardiac disorder.

Cardiac disease is a generic term that can be used interchangeably with the terms such as heart disease and cardiovascular disease. Cardiac disease in the present specification means every type of diseases that inhibit the normal functioning of the heart. More specifically, the diseases included in the cardiac disease in the present specification include coronary heart disease, cardiomyopathy, cardiovascular disease, ischemic heart disease, heart failure, hypertensive heart disease, inflammatory heart disease and valvular heart disease, but are not limited thereto.

In addition, one aspect of the present disclosure provides a composition for oxidizing fat or a composition for preventing or treating diseases associated therewith, in which the composition includes *Bacteroides acidifaciens* as an active ingredient. Another aspect provides a method for promoting fat oxidization or preventing or treating diseases associated therewith, in which the method includes administering *Bacteroides acidifaciens* to a subject in need of promotion of fat oxidization or prevention or treatment of diseases associated therewith. The method may further include, prior to administering, identifying a subject in need of promoting fat oxidization or prevention or treatment of diseases associated therewith. Another aspect provides a use of *Bacteroides acidifaciens* for the production of a pharmaceutical composition for promoting fat oxidation or preventing or treating disease associated therewith.

The composition for fat oxidation may be a pharmaceutical composition for preventing or treating a physiological or pathological condition induced by oxidative stress. In addition, the composition may be a pharmaceutical composition for preventing or treating physical or mental stress. The composition may be a pharmaceutical composition for preventing or treating one or more diseases selected from the group consisting of aging, cancer, multiple atherosclerosis, arthritis, Parkinson's disease, stroke, concussion, Alzheimer's disease, vascular disorders, hyperlipemia, myocardial infarction and cerebral infarction.

The composition for fat oxidation can be used not only for the metabolic diseases but also for the treatment of muscle diseases and related diseases such as sarcopenia, cachexia, muscle damage, muscular dystrophy and muscle fatigue, the improvement of muscle function and endurance, the improvement of body performance, the increase in endurance ability, the increase in muscle mass, the prevention of muscle loss, the increase in muscle recovery, the reduction of muscle fatigue, the improvement of energy balance, the maintenance of muscle performance and/or muscle strength and/or muscle mass and/or muscle function, the improvement of body shape, or the improvement of muscle:fat ratio.

In addition, one aspect of the present disclosure provides a composition for inhibiting DPP-4 or a composition for hypoglycemia, in which the composition includes *Bacteroides acidifaciens* as an active ingredient. Another aspect provides a method for inhibiting DPP-4 or hypoglycemia, in which the method includes administering *Bacteroides acidifaciens* to a subject in need of DPP-4 inhibition or hypoglycemia. The method may further include, prior to the administering, identifying a subject in need of DPP-4 inhibition or hypoglycemia. Another aspect provides a use of *Bacteroides acidifaciens* for use in the preparation of a pharmaceutical composition for inhibiting DPP-4 or hypoglycemia.

Dipeptidylpeptidase-4 (DPP-4) inhibitor is a medicament having a new mechanism for the regulation of blood glucose. Glucagon-like peptide-1 (GLP-1) and glucose-dependent insulinotropic polypeptide (GIP) are secreted in the gastrointestinal tract during food intake. It is called incretin, secreted in the K and L cells of the intestine, and degraded in the blood by the enzyme DPP-4 in a very short time. DPP-4 inhibitors increase the incretin blood level by inhibiting the DPP-4 enzyme responsible for the incretin degradation. In addition, the use of DPP-4 inhibitors has been shown to regulate blood glucose by stimulating insulin synthesis and secretion, inhibiting glucagon, and inhibiting glucose synthesis in the liver.

When the composition is prepared as a pharmaceutical composition for preventing or treating metabolic diseases or a fat oxidation-related disease, the composition may include a pharmaceutically acceptable carrier. Pharmaceutically acceptable carriers included in the composition are commonly used for the preparation, and include lactose, dextrose, sucrose, sorbitol, mannitol, starch, acacia rubber, calcium phosphate, alginate, gelatin, calcium silicate, microcrystalline cellulose, polyvinylpyrrolidone, cellulose, water, syrup, methylcellulose, methylhydroxybenzoate, propylhydroxybenzoate, talc, magnesium stearate and mineral oil, but are not limited thereto. The pharmaceutical composition may further include a lubricant, a wetting agent, a sweetening agent, a flavoring agent, an emulsifying agent, a suspending agent, a preservative, etc. in addition to the above ingredients.

The pharmaceutical composition for preventing or treating metabolic diseases or fat oxidation-related diseases may be administered orally or parenterally. In the case of parenteral administration, it can be administered by intravenous injection, subcutaneous injection, intramuscular injection, intraperitoneal injection, endothelial administration, topical administration, intranasal administration, intrapulmonary administration and intrarectal administration. In the case of oral administration, protein or peptide is digested and the oral composition should be formulated so as to coat the active agent or protect it from degradation in the stomach. In addition, the composition may also be administered by any device capable of transferring the active material to the target cell.

The subject of administration of the pharmaceutical composition may be an animal such as a mammal such as a human, or a cell, tissue, or culture thereof isolated therefrom.

The appropriate dosage of the pharmaceutical composition for preventing or treating metabolic diseases or fat oxidation-related diseases may be prescribed in various ways depending on factors such as a preparation method, an administration method, the age, body weight, gender, pathological condition of a patient, food, administration time, administration route, excretion speed, and responsiveness. The preferred dosage of the composition falls within the range of 100 to 100,000,000 ($10^2$ to $10^8$) cell/kg on an adult basis. The term "pharmaceutically effective amount" means an amount sufficient to prevent or treat a metabolic disease or a fat oxidation-related disease.

The composition may be prepared in unit dose form by using a pharmaceutically acceptable carrier and/or excipient according to a method which can be easily performed by those skilled in the art, or may be prepared by inserting it into a multi-dose container. At this time, the formulations may be in the form of solutions, suspensions, syrups or emulsions in oils or aqueous media, or in the form of extract, powders, powders, granules, tablets or capsules, and may additionally contain dispersing or stabilizing agents. In addition, the composition may be administered as an individual therapeutic agent or in combination with another therapeutic agent, and may be administered sequentially or simultaneously with a conventional therapeutic agent. It may also be administered once or additionally, if necessary.

*Bacteroides acidifaciens* according to the present disclosure may be utilized as a food composition. The food composition of the present disclosure may be easily used as a food, for example, main raw materials and supplementary raw materials of food, food additives, functional foods or beverages, which are effective for prevention and improvement of symptoms of metabolic diseases or for fat oxidation.

The term "food" in the present disclosure means a natural product or a processed product containing one or more nutrients, preferably a state of being able to be eaten directly through a certain degree of processing, and as an ordinary meaning, it includes all the food, food additives, functional foods and beverages.

Foods for which the composition for prevention or improvement of metabolic disease symptoms or for fat oxidization according to the present disclosure may include, for example, various foods, beverages, gums, tea, vitamin complexes and functional foods. In addition, in the present disclosure, the food may include special nutritional foods (e.g., milk formulas, baby food), meat products, fish meat products, tofu, jelled food, noodles (e.g., ramen, noodles), breads, dietary supplements, seasonings food (e.g., soy sauce, soybean paste, red pepper paste, and mixed soy paste), sauces, confectionery (e.g., snacks), candy, chocolate, gum, ice cream, milk products (e.g., fermented milk, cheese, etc.), other processed food, kimchi, pickled foods (various kinds of kimchi, pickled vegetables, etc.), beverages (e.g., fruit drinks, vegetable beverages, soy bean milk, fermented beverages, etc.) and natural seasonings (e.g., ramen soup), but are not limited thereto. The food, beverage or food additive may be prepared by a conventional preparation method.

In addition, the "functional food" means a food group imparted with added value to function or express the function of the corresponding food to a specific purpose by using physical, biochemical or biotechnological techniques in food, or to control the bio-defense rhythm of the food composition, or food which is designed and processed so as to sufficiently express the body's control function regarding the body, such as prevention of diseases and recovery, and the like, and specifically, it may be a health functional food. The functional food may include a food-acceptable food-aid additive, and may further include suitable carriers, excipients and diluents conventionally used in the preparation of functional foods.

In the present disclosure, the term "beverage" means a generic term for quenching thirst or for enjoying a taste, and includes a functional beverage. The beverage includes a composition for preventing or ameliorating the metabolic disease symptoms as an essential ingredient at the indicated ratio, and there is no particular limitation on the other ingredients. Various flavors or natural carbohydrates, such as ordinary beverages, may be contained as additional ingredients.

In addition to those described above, the food for preventing or ameliorating metabolic disease symptoms or containing the composition for fat oxidation of the present disclosure may contain various nutrients, vitamins, minerals (electrolytes), flavors such as synthetic flavors and natural flavors, coloring agents and fillers (cheese, chocolate, etc.), pectic acids and its salts, alginic acids and its salts, organic acids, protective colloid thickeners, pH adjusting agents, stabilizers, preservatives, glycerin, alcohol, and carbonation agents used for carbonated drink, and these ingredients may be used independently or in combination.

In the food containing the composition for preventing or ameliorating the metabolic disease symptoms of the present disclosure or for fat oxidation, the amount of the composition according to the present disclosure may be in the range of 0.001% by weight to 90% by weight, based on the total weight of the whole food, and may include preferably 0.1 to 40% by weight. In the case of beverages, they may be included in the ratio of 0.001 to 2 g, preferably 0.01 to 0.1 g, based on 100 ml. However, for health and hygiene purposes, a long-term intake for the purpose of health adjustment, the amount may be less than the above range. Since the active ingredient has no problem in terms of safety, it can be used in an amount exceeding the above range, but is not limited to the above range.

In addition, another aspect of the present disclosure provides a transformant expressing a lean phenotype, in which an Atg7 gene is deleted in dendritic cells. In addition, another aspect of the present disclosure provides a method for producing a transformant expressing a lean phenotype, in which the method includes deleting an Atg7 gene in dendritic cells.

In addition, another aspect of the present disclosure provides a pharmaceutical composition for preventing or treating metabolic diseases, in which the pharmaceutical composition includes Atg7, and an expression inhibitor or an activity inhibitor of a gene coding the same as active ingredients.

The expression inhibitor of the gene coding the Atg7 may be the gene-specific siRNA (small interference RNA), shRNA (short hairpin RNA), miRNA (microRNA), ribozyme, DNAzyme, PNA (peptide nucleic acids), and antisense oligonucleotides.

The activity inhibitor of Atg7 may be an antibody, an aptamer, a natural extract and chemicals specific for Atg7. The antibody may be a monoclonal antibody or a polyclonal antibody.

The term "transformation" in the present disclosure means a phenomenon that the genetic properties of an organism are changed by DNA given from the outside, that is, when DNA, which is a kind of nucleic acid extracted from cells of any system of an organism, is given to living cells of another system, the DNA enters into the cells to change genetic traits.

In the present disclosure, the term "transformant" means an individual produced by transformation, and is not limited to the individual, but preferably means a transformed animal.

In addition, another aspect of the present disclosure may provide a food composition for preventing or ameliorating metabolic diseases, in which the food composition includes Atg7, an expression inhibitor or an activity inhibitor of a gene coding the same as active ingredients.

In addition, one aspect of the present disclosure provides a method for screening useful intestinal microorganisms, in which the method includes comparing intestinal microorganisms of an individual of obesity or general phenotype with the transformant. The screening method may further include, after the comparing, selecting (determining) a microorganism having a large number of individuals in the transformant as useful intestinal microorganisms, as compared with intestinal microorganisms of an obese or general phenotype individual.

The useful intestinal microorganism may be a microorganism useful for metabolic diseases or fat oxidation, preferably a microorganism useful for lipid metabolic diseases.

Advantageous Effects

*Bacteroides acidifaciens* (BA) according to the present disclosure results in the activation of fat oxidation through the bile acid-TGR5-PPARα axis in adipose tissue, resulting in high energy consumption. At the same time, BA activates visceral DPP-4, followed by the increase in GLP-1, thereby contributing to glucose homeostasis. Bile acids, cholate and taurine also contribute to GLP-1 activity through a TGR5 receptor and improve insulin sensitivity. Accordingly, it can be used as a very effective therapeutic agent or prevention agent of metabolic diseases.

DESCRIPTION OF DRAWINGS

FIGS. 1A-1F are diagrams collectively showing a lean phenotype in an $Atg7^{\Delta CD11c}$ mouse.

FIG. 1A The body weight change of $Atg7^{f/f}$ and $Atg7^{\Delta CD11c}$ mice were monitored for 23 weeks (left panel). Body weight (middle panel) and fat mass (right panel) of 24-week-old male $Atg7^{f/f}$ and $Atg7^{\Delta CD11c}$ mice on a normal chaw diet (NCD). (n=8).

FIG. 1B Photographs of 24-week-old $Atg7^{f/f}$ and $Atg7^{\Delta CD11c}$ mice.

FIG. 1C Mill of abdominal adipose tissue of 24-week-old male $Atg7^{f/f}$ and $Atg7^{\Delta CD11c}$ mice on a NCD.

FIG. 1D Histological changes (left panel) and adipocyte size (right panel) in adipose tissue of $Atg7^{f/f}$ and $Atg7^{\Delta CD11c}$ mice. Scale bars=50 μm.

FIG. 1E Levels of glucose (right panel) and insulin (left panel) in the serum of $Atg7^{f/f}$ and $Atg7^{\Delta CD11c}$ mice on a NCD under non-fasting conditions.

FIG. 1F GTT (Glucose tolerance test; left panel) and ITT (insulin tolerance test; right panel) results for male $Atg7^{f/f}$ and $Atg7^{\Delta CD11c}$ mice.

All data are shown as mean±s.e.m. *P<0.05, P<0.01, and *P<0.001.

FIGS. 2A-2E are diagrams showing that a lean phenotype is originated from visceral symbiotic bacteria.

FIG. 2A Photographs of co-housing (CH; middle) and separated (left and right ends) 24-week-old male $Atg7^{f/f}$ and $Atg7^{\Delta CD11c}$ mice.

FIG. 2B Body weight (left panel) and fat mass (right panel) of 24-week-old male $Atg7^{f/f}$ and $Atg7^{\Delta CD11c}$ mice in a co-housing and a separated cage. (n=3 or 4).

FIG. 2C Results of monitoring the body weight of each mouse after co-housing (CH) for an additional 10 weeks (n=3 to 9).

FIG. 2D Body weight (left panel) and fat mass (right panel) of untreated B6 mice after 18 weeks of movement of feces in an $Atg7^{f/f}$ or $Atg7^{\Delta CD11c}$ mouse (n=5).

FIG. 2E Levels of glucose (right panel) and insulin (left panel) in the serum after movement of fecal extract of $Atg7^{f/f}$ or $Atg7^{\Delta CD11c}$ mouse under non-fasting conditions (n=5).

All data are mean±s.e.m values. *P<0.05, P<0.01, *P<0.001; ns, not significant.

FIGS. 3A-3D are diagrams collectively showing that *B. acidifaciens* (BA) is expanded in the feces of an $Atg7^{\Delta CD11c}$ mouse in visceral symbiotic bacteria.

FIG. 3A Phylum level detected by pyrosequencing.

FIG. 3B Pyrosequencing data (n=6) from the class to the genus (left to right).

FIG. 3C Representative graphs of species representing the distribution of BA in the feces detected by pyrosequencing. Red arrow=BA.

FIG. 3D IECs (intestinal epithelial cells) of $Atg7^{f/f}$ and $Atg7^{\Delta CD11c}$ mice determined by BA-specific FISH (fluorescence in situ hybridization) probe and the number of BA increased in lumens of colon (n=3). Scale bar=100 μm. All data are mean±s.e.m values. *P<0.05; ns, not significant.

FIGS. 4A-4F are diagrams collectively showing that *B. acidifaciens* (BA) regulates the body weight and fat mass of diet-induced B6 mouse obesity.

FIG. 4A Photographs of high-fat diet (HFD; left panel) and PBS- and BA-fed mice. The body weight of each group was monitored for 10 weeks (right panel). BA was orally administered ($5 \times 10^9$ CFU/100 μl) (n=5).

FIG. 4B Oral dietary intake with PBS or BA (n=5).

FIG. 4C MRI of PBS- and BA-fed mice.

FIG. 4D Histological changes in adipose tissue (left panel) and adipocyte size (right panel) of PBS- and BA-fed mice in HFD.

All data are shown as mean±s.e.m of ≥2 independent experiments.

FIG. 4E Results of GTT (glucose tolerance test; left panel, n=8 or 9) and ITT (insulin tolerance test; right panel, n=7-12) using the serum of PBS- and BA-fed mice measured at a certain point after intraperitoneal injection of glucose or insulin.

FIG. 4F Energy consumption (top left panel), total activity (top right panel), and RER (respiratory exchange ratio; bottom left panel) (n=5) of PBS- or BA-fed mice. All data are expressed as mean±s.e.m. *P<0.05, P<0.01, *P<0.001; ns, not significant.

FIGS. 5A-5E are diagrams collectively showing that *B. acidifaciens* (BA) induces fat oxidation in adipose tissue through PPARα activity.

FIG. 5A At the end of each experiment, the expression levels of mRNAs of genes related to fatty acid synthesis (FasN, HSL, PEPCK, SCD1, and PPARγ), β-oxidation (PPARα), thermogenesis (PRDM16, PGC1a, Cidea, and GLUT4) were determined through real-time PCR using the epididymis adipose tissues of $Atg7^{f/f}$ and $Atg7^{\Delta CD11c}$ mice (n=5).

FIG. 5B The expression levels of mRNAs of genes related to fatty acid synthesis (FasN, HSL, PEPCK, SCD1, and PPARγ), β-oxidation (PPARα), thermogenesis (PRDM16, PGC1a, Cidea, and GLUT4) were determined through real-time PCR using the epididymis adipose tissues of mice transplanted with fecal microorganisms (n=5).

FIG. 5C The expression levels of mRNAs of genes related to fatty acid synthesis (FasN, HSL, PEPCK, SCD1, and PPARγ), β-oxidation (PPARα), thermogenesis (PRDM16, PGC1a, Cidea, and GLUT4) were determined through real-time PCR using the epididymis adipose tissues of BA-fed mice (n=5).

FIG. 5D The PPARα expression level in adipose tissue after 1, 7 and 14 days of daily BA administration were analyzed through RT-PCR.

FIG. 5E The TGR5 expression level in adipose tissue after 1, 7 and 14 days of daily BA administration were analyzed through RT-PCR.

All data are mean±s.e.m of ≥2 independent experiments. *P<0.05, P<0.01, *P<0.001; ns, not significant.

FIGS. 6A-6D are diagrams collectively showing that *B. acidifaciens* (BA) regulates DPP-4 (dipeptidal peptidase-4) secretion to induce GLP-1 production.

FIG. 6A Levels of glucose (right panel) and insulin (left panel) in the serum of PBS- and BA-fed mice (normal chow diet, NCD; high-fat diet, HFD).

FIG. 6B Levels of activated GLP-1 in the serum of PBS- and BA-fed mice (normal chow diet, NCD; high-fat diet, HFD; n=5).

FIG. 6C One hour after administration of BA or BA culture supernatant or medium alone to untreated B6 mice, the level of DPP-4 in the small intestine was confirmed by light emission analysis.

FIG. 6D Quantification of cholates (left panel) and taurine (right panel) in the feces of PBS- and BA-fed mice (n=5) using CE-MS (Capillary Electrophoresis Mass Spectrometry).

All data are mean±s.e.m of ≥2 independent experiments. *P<0.05, P<0.01, *P<0.001; ns, not significant.

FIG. 7 is a diagram showing a mechanism by which *B. acidifaciens* (BA) can prevent or treat insulin sensitivity and obesity.

Specific visceral symbiotic bacteria (i.e., BA) expanded in a lean phenotype $Atg7^{\Delta CD11c}$ mouse were identified. Administration of BA results in the activation of fat oxidation through the bile acid-TGR5-PPARα axis in adipose tissue, resulting in high energy consumption. At the same time, BA activates visceral DPP-4, followed by the increase in GLP-1, thereby contributing to glucose homeostasis. Bile acids, cholate and taurine also contribute to GLP-1 activity through a TGR5 receptor and improve insulin sensitivity.

PPARα, peroxisome proliferator-activated receptor α; SCFAs, short-chain fatty acids.

FIG. 8 is a diagram showing that an $Atg7^{\Delta CD11c}$ mouse shows a lean phenotype regardless of gender.

Body weight of male (FIG. 8 left panel) and female (FIG. 8 right panel) $Atg7^{f/f}$ and $Atg7^{\Delta CD11c}$ mice between 7 and 23 weeks of age on a NCD.

FIGS. 9A-9C are diagrams showing that the lean phenotype of 24-week-old $Atg7^{\Delta CD11c}$ mouse is not associated with inflammation.

FIG. 9A Levels of pre-inflammatory cytokines in the serum of $Atg7^{f/f}$ and $Atg7^{\Delta CD11c}$ mice (n=7) measured using a cytometric bead array mouse-inflammatory kit (BD Biosciences).

FIG. 9B F4/80 (left panel) and TNFα (right panel) mRNA expression levels through real-time PCR.

FIG. 9C Results of hematoxylin eosin staining of small intestine (top panels) and colon (bottom panels). Scale bar=100 μm.

All data are mean±s.e.m in 2 independent experiments. *P<0.05; ns, not significant.

FIGS. 10A-10B are diagrams showing OPLS-DA (Orthogonal partial least squares discriminate analysis) of fecal metabolites of $Atg7^{f/f}$ and $Atg7^{\Delta CD11c}$ mice.

FIG. 10A Cross-validated score plots from OPLS-DA of 1H-NMR (nuclear magnetic resonance) in the feces of $Atg7^{f/f}$ and $Atg7^{\Delta CD11c}$ mice (n=7).

FIG. 10B S-plot for the predicted components from OPLS-DA of 1H-NMR data in the feces of $Atg7^{f/f}$ and $Atg7^{\Delta CD11c}$ mice (n=7).

FIG. 10C Quantification of short chain fatty acids in the feces of $Atg7^{f/f}$ and $Atg7^{\Delta CD11c}$ mice (n=5) using gas chromatography-mass spectrometry (e.g., left to right: acetates, butyrates and propinate) and lactate (far right panel). All data are mean±s.e.m. *P<0.05, **P<0.01.

FIG. 11 is a diagram showing compensated body weight changes of a mouse of the same kind in co-housing (CH) cage and fecal microorganisms.

The body weight of Atg7$^{f/f}$ (n=5) and Atg7$^{\Delta CD11c}$ (n=4) mice in a CH cage and the body weight of Atg7$^{f/f}$ and Atg7$^{\Delta CD11c}$ mice (S) raised separately are shown by a line graph based on gray and blue circles, respectively.

FIG. 12 is a diagram showing that pyrosequencing data at the species level in the feces of an Atg7$^{\Delta CD11c}$ mouse shown in FIG. 3C show a color legend.

FIG. 13 is a diagram showing the biological arrangement of *Bacteroides* contig in the DNA metagenome.

The relative abundance of the number of contigs in the feces of Atg7$^{f/f}$ and Atg7$^{\Delta CD11c}$ mice are compared. All data are shown as mean±s.e.m. * P<0.05; ***P<0.001; ns, not significant.

FIGS. 14A-14B are diagrams collectively showing that *B. acidifaciens* (BA) that are orally administered remains in the colon temporarily.

Colons and feces were obtained at nil and after 1-5 days after oral administration of BA (5×10$^9$ CFU/100 μl), and stained with BA-specific FISH (fluorescence in situ hybridization) probes.

FIG. 14A The confocal image of the BA (yellow arrow).

FIG. 14B Quantification of BA in the feces at a specific point of time. The number was counted at 20 sites per slide. All data are shown as mean±s.e.m of three independent experiments. ***P<0.001; N.D., not detected.

FIGS. 15A-15F are diagrams collectively showing the effective function of the body weight and fat mass of *B. acidifaciens* (BA) in NCD-fed B6 mice provided with BA or PBS.

FIG. 15A Photographs and body weight after 10 weeks (left and right panels, respectively). BA was orally administered daily (5×10$^9$ CFU/100 μl).

FIG. 15B Oral dietary intake with PBS or BA.

FIG. 15C MRI analysis.

FIG. 15D Histological changes of adipose tissues (left panel) and changes in adipocyte size (right panel).

FIG. 15E Results of GTT (glucose tolerance test) (left panel, n=8 or 9) and ITT (insulin tolerance test) (right panel, n=7-12) at a specific point of time after intraperitoneal injection of glucose or insulin.

FIG. 15F Energy consumption (left panel), total activity (middle panel), and RER (respiratory exchange ratio; right panel) of PBS- or BA-fed mice (n=5).

All data are shown as mean±s.e.m. *P<0.05, P<0.01, *P<0.001; ns, not significant.

FIGS. 16A-16B are diagrams showing that mice fed with NCD or HFD and *B. sartorii* (BS) have similar body weight and dietary intake.

FIG. 16A Body weight for 10 weeks after oral administration of BS (n=5) (5×10$^9$ CFU/100 μl).

FIG. 16B Dietary intake. Data are mean±s.e.m. of two independent experiments. ns, not significant.

FIG. 17 is a diagram showing that the administration of *B. acidifaciens* (BA) improves liver and peripheral insulin sensitivity.

It is the result of performing hyperinsulinemic-euglycemic clamp for BA-, heat-inactivated BA-fed mice and NCD-fed control mice (n=3) for 6 weeks. During the clamp experiment, the amount of insulin solution was determined to be 3 mU based on the first experiment. The inhibition of systemic glucose uptake (peripheral insulin sensitivity, FIG. 17 left panel) and insulin-mediated liver glucose production (liver insulin sensitivity, FIG. 17 right panel) were significantly increased in BA-fed mice as compared to heat inactivated BA-fed group. All data are shown as mean±s.e.m. *P<0.05; ns, not significant.

FIGS. 18A-18B are diagrams showing the levels of SCFAs (short-chain fatty acids) and lactate levels in the feces after oral administration of *B. acidifaciens* (BA) for 10 weeks.

FIG. 18A Levels of acetate, butyrate, propionate, and lactate in the feces of mice with NCD (panels from left to right; n=5) were measured through gas chromatography-mass spectrometry. All data are mean±s.e.m. *P<0.01; ns, not significant.

FIG. 18B Levels of acetate, butyrate, propionate, and lactate in the feces of mice with HFD (panels from left to right; n=6) were measured through gas chromatography-mass spectrometry. All data in FIGS. 18A-18B are mean±s.e.m. *P<0.01; ns, not significant.

FIGS. 19A-19B are diagrams showing the similar levels of lipid metabolism in liver and small intestine in Atg7$^{f/f}$ and Atg7$^{\Delta CD11c}$ mice.

FIG. 19A The expression levels of mRNAs of genes related to fatty acid synthesis (FasN, HSL, PEPCK, SCD1, and PPARγ), β-oxidation (PPARα), thermogenesis (PRDM16, PGC1a, Cidea, and GLUT4) were determined through real-time PCR using liver of Atg7$^{f/f}$ and Atg7$^{\Delta CD11c}$ mice (FIG. 19A; n=5). All data are mean±s.e.m.

FIG. 19B The expression levels of mRNAs of genes related to fatty acid synthesis (FasN, HSL, PEPCK, SCD1, and PPARγ), β-oxidation (PPARα), thermogenesis (PRDM16, PGC1a, Cidea, and GLUT4) were determined through real-time PCR using small intestine of Atg7$^{f/f}$ and Atg7$^{\Delta CD11c}$ mice. All data are mean±s.e.m.

FIGS. 20A-20B are diagrams showing that *B. acidifaciens* (BA) does not induce β-cell hyperpolarization.

Pancreatic tissues were obtained from mice (n=5) administered with (5×10$^9$ CFU/100 μl) for 10 weeks.

FIG. 20A The confocal image of the pancreatic islet (α-cells are red, β-cells are green). Scale bar=50 μm. Sections were continuously reacted with mouse anti-glucagon IgG Ab (K79bB10; Sigma-Aldrich, St. Louis, Mo.) and rabbit polyclonal anti-insulin Ab (Santa Cruz Biotechnology, Santa Cruz, Calif.), they were reacted with PE-conjugated anti-mouse IgG (eBioscience, San Diego, Calif.) and FITC-conjugated anti-rabbit IgG (eBioscience, San Diego, Calif.), respectively.

FIG. 20B The size of a β-cell region was quantified using an ImageJ software program. The pancreatic islets were randomly selected as 10 sites per slide. All data are mean±s.e.m. ***P<0.001; ns, not significant.

FIGS. 21A-21C are graphs showing triglyceride and cholesterol levels in plasma of Atg7$^{\Delta CD11c}$, fecal microbiota transplantation (FMT), and *B. acidifaciens* (BA)-fed mice.

FIG. 21A The concentrations of plasma triglycerides and total cholesterol were analyzed by using an enzyme assay kit in Atg7$^{\Delta CD11c}$ mice (n=3). All data are mean±s.e.m. ns, not significant.

FIG. 21B The concentrations of plasma triglycerides and total cholesterol were analyzed by using an enzyme assay kit in FMT mice (n=5). All data are mean±s.e.m. ns, not significant.

FIG. 21C The concentrations of plasma triglycerides and total cholesterol were analyzed by using an enzyme assay kit in BA-fed mouse (n=5). All data are mean±s.e.m. ns, not significant. NCD, normal chow diet; HFD, high-fat diet.

FIG. 22 is a diagram showing that *B. acidifaciens* (BA) can regulate self-digestion of CD11c$^+$ cells.

The number of BA in bone marrow-derived CD11c$^+$ cells after 6 and 24 hours of co-incubation with BA were determined on EG agar plates (MOI=10). Bone marrow was obtained from Atg7$^{f/f}$ and Atg7$^{\Delta CD11c}$ mice. All data are mean±s.e.m of three independent experiments. * P<0.05; N.D., not detected.

MODES OF THE INVENTION

Hereinafter, the present disclosure will be described in more detail by way of examples. However, these examples are for illustrative purposes only, and the scope of the present disclosure is not limited to these examples.

Example 1: Animal Experiment

All animal experiments were approved by the Asian Animal Experimental Ethics Committee (permit number: PN 2014-13-069). All experiments were performed under anesthesia with ketamine (100 mg/kg) and xylazine (20 mg/kg).

Example 2: Mice and Bacteria Strain

C57BL/6 (B6), and CD11c-Cre, Villine-Cre, and LysM-Cre mice were purchased from Charles River Laboratories (Orient Bio Inc., Sungnam, Korea) and Jackson Laboratory (Bar Harbor, Me.). ATG7$^{flox/flox}$ mice were provided by Masaaki Komatsu (Tokyo Metropolitan Institute of Medical Science, Japan). Atg7$^{\Delta CD11c}$ mice were prepared by cross-breeding CD11c$^{cre}$ mice and ATG7$^{f/f}$ mice in the animal laboratory of Seoul Asian Medical Center. All mice were fed with sterile feed and drinking water under non-pathogenic conditions. *B. acififaciens* (JCM10556) and *B. sartorii* (JCM17136) were purchased from Japan Collection of Microorganisms (JCM) of RIKEN BioResource Center.

Example 3: 454 Pyrosequencing Analysis cDNA was extracted from the feces using QIAamp DNA stool mini kits (Qiagen, Valencia, Calif.). PCR amplification was performed using primers targeting the V1 to V3 sites of 16S rRNA gene. For the amplification of bacteria, primer 9F

```
                                     SEQ ID NO: 1
(5'-CCTATCCCCTGTGTGCCTTGGCAGTC-TCAG-AC-

AGAGTTTGATCMTGGCTCAG-3';
``` the underlined sequence means primer at the target site) to which a barcode is attached and 541R

```
                                     SEQ ID NO: 2
(5'-CCATCTCATCCCTGCGTGTCTCCGAC-TCAG-X-AC-

ATTACCGCGGCTGCTGG-3';
```

'X' means a specific barcode of each object) (oklbb_ezbio-cloud_net/content/1001) were used.

Amplification was performed under the following conditions: initiation of denaturation at 95° C. for 5 minutes, 30 cycles denaturation at 95° C. for 30 seconds, primer annealing at 55° C. for 30 seconds, and amplification at 72° C. for 30 seconds, and final extension at 72° C. for 5 minutes. The same concentrations of the presumed products were pooled together and short pieces (non-target objects) were removed using an AMPure bead kit (Agencourt Bioscience, Beverly, Mass.). The quality and size of the products were measured on Bioanalyzer 2100 (Agilent, Palo Alto, Calif.) using DNA 75001 chip. Sequencing of the mixed amplifications was performed via emulsion PCR, and then was placed on a picotiter plate. Sequencing was performed on Chunlab (Seoul, Korea) on the GS Junior Sequencing System (Roche, Branford, Conn.). Pyrosequencing data analysis was performed according to the prior art (Lim Y. W. et al.).

Example 4: Measurement of CE-TOF-MS (Capillary Electrophoresis (CE) Time-of-Flight Mass Spectrometry)

Quantitative analysis of the charged metabolites using CE-TOF-MS was performed as follows. 10 mg of lyophilized fecal samples were milled using 3-mm zirconia-silica beads (BioSpec Products, Bartlesville, Okla.), and as an internal standard, they were homogenized using 400 µl of MeOH containing 20 µM each of methionine sulfone (Wako, Osaka, Japan) as a cation, IVIES (Dojindo, Kumamoto, Japan) as an anion, and CSA (D-Camphol-10-sulfonic acid; Wako). Subsequently, 200 µl of de-ionized water and 500 µl of chloroform were added. By using a Shakemaster neo (Bio Medical Science, Tokyo, Japan), they were stirred in 1,500 r.p.m. for 10 minutes, the solution was centrifuged at 4,600 g for 15 minutes at 4° C., and the protein was removed by filtering using a Millipore 5,000-Da cut-off filter (Millipore, Billerica, Mass.). The filtrate was lyophilized and dissolved in 25 µl water containing 200 µM each of 3-aminopyrrolidine (Sigma-Aldrich) and trimesate (Wako) as reference compounds. All CE-TOF-MS experiments were conducted using Agilent Technologies equipment: CE capillary electrophoresis system, G3250AA LC/MSD TOF system, 1100 series binary HPLC pump, G1603A CE-MS adapter, and G1607A CE-ESI-MS sprayer kit. Data were treated (MasterHands) using internal software (Sugimoto M et al.) to determine peak annotation and quantification.

Example 5: Gas Chromatography Mass Spectrometry (GC-MS) Measurement

The organic concentration in the feces was determined by gas chromatography-mass spectrometry. A partial sample (80 ml) of the ether extract of the feces was mixed with N-tert-butyldimethylsilyl-Nmethyltrifluoroacetamide. The vial was sealed, heated in boiling water at 80° C. for 20 minutes, and then placed at room temperature for 48 hours for derivatization. The derivatized samples were treated with a 6890N Network GC System (Agilent Technologies) equipped with an HP-5MS column (0.25 mm×30 m×0.25 mm) and a 5973 Network Mass Selective Detector (Agilent Technologies).

Pure helium (99.9999%) was used as carrier gas and was delivered at a rate of 1.2 ml min$^{-1}$.

The outlet pressure was set at 97 kPa divided by 20:1. The inlet and travel line temperatures were 250 and 260° C., respectively. The temperature program was used as follows: 60° C. (3 minutes), 60-120° C. (5° C./min), 120-300° C. (20° C./min). Subsequently, 1 µl of each sample was injected for a reaction time of 30 minutes. The organic acid concentration was quantified by comparing the peak area with the standard.

Example 6: Measurement of GLP-1 (Glucagon-Like Peptide-1)

Blood samples were obtained from a control group and BA-fed mice, and were centrifuged at 1800 g at 4° C. for 30 minutes. DPP-4 (dipeptidyl peptidase-4) inhibitor was added and GLP-1 concentration was determined using GLP-1 ELISA kit (Shibayagi).

Example 7: Measurement of DPP-4

DPP-4 levels were measured. After 6 hours of fasting in wild-type B6 mice, BA (5×10$^9$ CFU/100 µl) or its culture supernatant (100 µl/head) or culture medium alone was administered with DPP-4 inhibitor sitagliptin (40 mg/mouse; Merck Sharp Dohme and Chibret Laboratories, Rahway, N.J.) followed by glucose for 30 minutes. After 15 minutes, intestinal epithelial cells of the ileum were recovered from pretreated mice and washed with PBS to remove luminal materials. Mucus was scraped off, epithelium was cut into 1-2 mm in length, and placed in 1 ml PBS. The sliced tissues was spun down to centrifugation (6,000 g, 4° C., 5 min), and 50 µl of supernatant was incubated using DPP-4 Glo protease assay (Promega, Madison, Wis.) at 37° C. for 2 hours together with kit reagents. DPP-4 activity was calculated as the value of a control sample in the absence of sitagliptin.

Example 8: Statistics

GraphPad Prism software (GraphPad, La Jolla, Calif.) was used for statistical analysis. Significant differences between the two groups were analyzed by two-tailed paired t-test or Mann-Whitneyt t-test. A plurality of groups were analyzed using two-way ANOVA followed by Bonferroni post-hoc test (*, P<0.05; , P<0.01; *, P<0.001).

Example 9: Identification of Reduced Body Weight and Fat Mass in Atg7$^{\Delta CD11c}$ Mice In order to identify the role of immune cell self-digestion action in the occurrence of metabolic diseases, the body weight and action were observed in dendritic cells (Atg7$^{\Delta CD11c}$), alimentary canal epithelial cells (Atg7$^{\Delta villin}$), and macrophages (Atg7ΔLysM) of Atg7 conditional knock-out mice. The mice were fed with NCD (normal chow diet). Thereafter, it was confirmed that the difference in body weight between the Atg7$^{\Delta CD11c}$ mice and their litter control group mice (Atg7$^{flox/flox\ (f/f)}$) was increased (FIG. 1A).

Importantly, it was confirmed that 24-week-old Atg7$^{\Delta CD11c}$ mice had very low body weight and fat mass as compared to Atg7$^{f/f}$ mice (FIGS. 1A and 1B). A lean phenotype (Atg7$^{\Delta CD11c}$; FIG. 8) is shown both in females and males.

In MRI (Magnetic Resonance Imaging) analysis, abdominal adipose tissues that were remarkably reduced in Atg7$^{\Delta CD11c}$ mice were confirmed in both axial and coronal directions as compared to their litter Atg7$^{f/f}$ mice (FIG. 1C). In addition, the single adipocyte size of visceral adipose tissue obtained from Atg7$^{\Delta CD11c}$ mice was significantly small as compared to Atg7$^{f/f}$ mice (FIG. 1D).

In order to confirm the involvement of systemic or mucosal inflammation in Atg7$^{\Delta CD11c}$ mice of a lean phenotype, the level of proinflammatory cytokine in serum and mRNA expression of F4/80 and TNFα in visceral adipose tissue were confirmed, and the tissues of the small intestine and colon were analyzed. It was confirmed that Atg7$^{\Delta CD11c}$ mice showed similar or decreased levels of multiple markers of systemic and mucosal inflammation indicating that the lean phenotype of Atg7$^{\Delta CD11c}$ mice was not related to inflammation (FIGS. 9A and 9B).

Importantly, higher insulin and subsequent low glucose levels than Atg7$^{f/f}$ mice under non-fasting conditions were identified in the serum of Atg7$^{\Delta CD11c}$ mice (FIG. 1E). It was confirmed that the insulin resistance determined by GTT (glucose tolerance test) and ITT (insulin tolerance test) in Atg7$^{\Delta CD11c}$ mice as compared to the litter Atg7$^{f/f}$ was improved in Atg7$^{\Delta CD11c}$ mice as compared to the litter Atg7$^{f/f}$ (FIG. 1F). To sum up, these data indicate that Atg7$^{\Delta CD11c}$ mice have reduced fat mass and improved glucose homeostasis.

Example 10: Identification of Low SCFAs Levels in the Feces of Atg7$^{\Delta CD11c}$ Mice Since aged Atg7$^{\Delta CD11c}$ mice have low body weight and fat mass, the relevance between a lean phenotype and energy use was confirmed using CE-TOF-MS (capillary electrophoresis time-of-flight mass spectrometry) of Example 4 and GC-MS (gas chromatography mass spectrometry) of Example 5 in the feces.

Individual plots of Atg7$^{\Delta CD11c}$ mice in OPLS-DA (orthogonal partial least squares discriminant analysis) are clearly distinct from Atg7$^{f/f}$ mice (FIG. 10A).

Furthermore, some SCFAs such as acetate, butyrate, propionate and lactate are located at the remote spot from the axis (FIG. 10B), which indicates that these factors contribute to distinguish Atg7$^{f/f}$ and Atg7$^{\Delta CD11c}$ mice. In reality, the amount of acetate, butyrate, and propionate in Atg7$^{\Delta CD11c}$ mice was remarkably reduced as compared to Atg7$^{f/f}$ mice, whereas the amount of lactate was higher (FIG. 10C).

Example 11: Identification that Symbiotic Bacteria are Related to a Lean Phenotype of Aged Atg7$^{\Delta CD11c}$ Mice In order to confirm whether a lean phenotype of Atg7$^{\Delta CD11c}$ mice is related to symbiotic bacteria, co-housing (CH) and FMT (fecal microbiota transplantation) experiments were performed. From birth, Atg7$^{\Delta CD11c}$ and Atg7$^{f/f}$ mice shared a cage and exposed feces.

As a result, Atg7$^{f/f}$ mice that shared the cage with Atg7$^{\Delta CD11c}$, lost more both body weight and fat as compared to Atg7$^{f/f}$ mice (FIGS. 2A and 2B; FIG. 11). In addition, Atg7$^{\Delta CD11c}$ mice that shared the cage with Atg7$^{f/f}$ mice increased body weight and fat compared to Atg7$^{\Delta CD11c}$ mice (FIGS. 2A, and 2B; FIG. 11). In order to confirm whether the phenotype of CH mice was due to symbiotic microorganisms, mice were transferred to their respective cages after co-housing experiments. As shown in FIG. 2C, Atg7$^{\Delta CD11c}$ mice lost body weight when they were raised alone, whereas Atg7$^{f/f}$ mice did not. In addition, the oral administration of the fecal extract of Atg7$^{\Delta CD11c}$ mice to wild-type B6 mice for 12 weeks resulted in significantly lower body weight and fat mass than the feces of wild type B6 or Atg7$^{f/f}$ mice (FIG. 2D). In addition, importantly, wild-type B6 mice to which the fecal extract of Atg7$^{\Delta CD11c}$ mice is administered showed higher insulin levels and subsequent low serum glucose levels as compared to the mice to which the extract of Atg7$^{f/f}$ is administered (FIG. 2E).

To sum up, these results indicate that they play an essential role in the lean phenotype of Atg7$^{\Delta CD11c}$ mice.

Example 12: Expansion of *Bacteroides acidifaciens* (BA) in the Feces of Atg7$^{\Delta CD11c}$ Mice Metagenomics analysis was used to confirm the diversity and composition of intestinal symbiotic bacteria. In pyrosequencing analysis, it was confirmed that the faces of Atg7$^{f/f}$ and Atg7$^{\Delta CD11c}$ mice were mutually similar in the primary distribution of intestinal microorganisms at the Bacteroidetes, Firmicutes, and Proteobacteria ratios, and phylum level (FIG. 3A). There was no similar or significant difference in the distribution of Bacteroidia (class), Bacteroidales (order), Bacteroidaceae (family), and *Bacteroides* (genus) (FIG. 3B). However, at the species level, it was confirmed that the ratio of BA was significantly extended in the feces of Atg7$^{\Delta CD11c}$ mice as compared to Atg7$^{f/f}$ mice (5.48±1.76% vs. 0.77±0.18%) (FIG. 3C, red arrow; FIGS. 12 and 13).

On the other hand, there was no difference in the ratio of the other *Bacteroides* species including *B. sartorii* in the feces of Atg7$^{\Delta CD11c}$ or Atg7$^{f/f}$ mice (FIG. 13).

In alpha diversity, the species abundance of the fecal microorganisms of Atg7$^{\Delta CD11c}$ mice (Chao 1 index) was remarkably reduced, whereas the biodiversity (Shannon/Simpson index) was similar to the fecal microorganism of Atg7$^{f/f}$ mice (Table 1 below).

|  | Chao1 | Shannon | Simpson Reciprocal |
|---|---|---|---|
| Atg7$^{f/f}$ | 932.13 ± 109.72 | 4.39 ± 0.43 | 0.04 ± 0.02 |
| Atg7$^{\Delta CD11c}$ | 604.41 ± 203.83 | 4.28 ± 0.28 | 0.04 ± 0.03 |

FISH (fluorescence in situ hybridization) analysis was performed to confirm the expansion of BA in Atg7$^{\Delta CD11c}$ mice of a lean phenotype. As shown in FIG. 3D, the number of increased BA was detected in the lumen of the colon, and it was confirmed that a small amount of BA was internalized into the colon epithelial cells of Atg7$^{\Delta CD11c}$ mice.

To sum up, these results indicate that, in symbiotic bacteria, BA has been expanded in lean phenotype intestines.

Example 13: Identification that the Oral Administration of BA to High Fat Diet (HFD)-Provided B6 Mice Induces a Lean Phenotype In order to confirm whether extended BA regulates lipid metabolism, BA (JCM10556) was obtained and cultured to obtain large amounts of microorganisms, which were provided to untreated B6 mice.

In order to determine the optimal conditions of administration, colon tissues and BA in mice fed with BA (5×10$^9$ CFU/100 µl) were quantitated by FISH analysis. One day after oral administration, a large number of BA were detected in the lumen of colon epithelial cells (FIG. 14A). After 2 days of oral administration, the number of BA in the peak feces subsequently disappeared and recovered rapidly (FIG. 14B). It was confirmed that the oral administration of BA reduced body weight and fat mass of wild-type B6 mice provided with NCD and HFD without dietary effects (FIGS. 4A-4C; FIGS. 15A-15C). In contrast, no body weight loss was observed in *B. sartorii*-provided mice used as control groups (FIG. 16A). In addition, the size of single adipocytes in adipose tissue of the epididymal was significantly lower in BA- and HFD-provided B6 mice as compared to PBS- and HFD-provided mice (FIG. 4D). In addition, the insulin resistance determined by GTT and ITT improved remarkably in BA- and HFD-provided mice as compared to PBS- and HFD-provided mice (FIG. 4E).

A hyperinsulinemic-euglycemic clamp technique using heat-inactivated BA as a control group was used to confirm the effect of BA feeding on liver and peripheral insulin sensitivity.

Interestingly, the BA feeding improved liver and peripheral insulin sensitivity (FIG. 17). It was confirmed that the oral administration of BA showed a decrease in butylate in the feces of NCD-fed mice, but it was confirmed that levels of acetate, propionate, and lactate were not changed (FIG. 18A). A similar trend was confirmed in the HFD-fed group (FIG. 18B). In order to measure energy consumption, activity and substrate utilization, the mice provided with BA were monitored after they were individually raised in a CLAMS (a comprehensive laboratory animal monitoring system) cage for 5 days. It was confirmed that the group of PBS or BA-provided mice showed a similar locomotor activity and respiratory exchange ratio, whereas BA- and HFD-fed mice consumed more energy as compared to PBS- and HFD-fed mice (FIG. 4F). The NCD-fed mice to which oral BA is administered showed a similar effect (FIG. 15F).

To sum up, the long-term administration of BA induces energy consumption, and accordingly, causes a lean phenotype of dominance in diet-induced obese mice.

Example 14: Identification that a Lean Phenotype Mouse Shows an Increase in PPARα (Peroxisomeproliferator-Activated Receptor α) Expression in Adipose Tissues Expression levels of genes related to lipid metabolism in adipose tissue, liver, and small intestine were analyzed based on the detection of decreased body weight and fat mass in Atg7$^{\Delta CD11c}$, FMT B6, and BA-fed B6 mice. Importantly the expression of genes related to lipid β-oxidation, particularly PPARα, increased only in adipose tissue of the epididymis of Atg7$^{\Delta CD11c}$ mice (FIG. 5A). No significant difference could be identified in the small intestine and liver (FIGS. 19A and 19B). To be consistent with these results, PPARα expression was significantly up-regulated in adipose tissue of the epididymis of B6 mice fed with the fecal extract of Atg7$^{\Delta CD11c}$ and mice fed with HFD and BA for 10 weeks (FIGS. 5B and 5C).

The level of PPARα expression in B6 mice by BA administration by the time-dependent method was measured to confirm whether the enhanced β-oxidation level was activated by the bacteria alone or was not activated by the product of a lean phenotype.

Interestingly, the level of mRNA of PPARα in epididymis adipose tissue of B6 mice was significantly increased after 2 weeks of BA administration (FIG. 5D).

In addition, the expression levels of TGR5, GPBAR1 (G-protein-coupled bile acid receptor), which can stimulate energy consumption through PPARα activity, were measured.

As a result, it was confirmed that BA administration increased the level of TGR5 expression in adipose tissue (FIG. 5E). These results indicate that a lean phenotype by BA initiates fat oxidation in adipose tissue according to TGR5-PPARα activity.

Example 15: Identification that BA Mediates Production of GLP-1 (Glucagon-Like Peptide-1) by Regulation of DPP4 (Dipeptidylpeptidase-4) and Production of Bile Acids The role of BA in glucose homeostasis was confirmed. As expected, BA-fed B6 mice showed higher insulin and lower glucose levels in serum than PBS-fed B6 mice (FIG. 6A).

In order to confirm whether this increase in plasma insulin levels was due to over-stimulation of β-cells, α and β cells were stained in pancreatic tissue 10 weeks after BA feeding.

As a result, it was confirmed that the BA feeding did not induce hypersensitivity of β-cells (FIGS. 20A and 20B).

In order to confirm the mechanism of high levels of insulin secretion in BA-fed lean mice, levels of GLP-1 stimulating insulin release into the blood were measured.

GLP-1 levels in serum were remarkably increased in NCD and HFD-fed mice (FIG. 6B).

It was confirmed that the level of DPP-4, a well-known enzyme with inhibiting activity of GLP-1, decreased in the small intestine and ileum after oral administration of BA or its culture supernatant (FIG. 6C).

In addition, DPP-4 activity was measured, reflecting the amount of protein. Previous studies have shown that bile juice plays a key role in glucose homeostasis through stimulation of GLP-1 secretion through TGR5 activity.

As a result, it was confirmed a significantly increased level of deconjugated cholate, salt of cholic acid, and taurine from primary bile acid in the feces of B6 mice fed with BA for 10 weeks, but significant loss of cholesterol could not be confirmed (FIG. 6D; FIG. 21C). These results indicate that BA or its metabolites lower the activity of the DPP-4 enzyme, and accordingly, causing GLP-1 activity, thereby improving insulin sensitivity and glucose resistance.

To sum up, the present inventors have confirmed that the specific intestinal symbiotic bacteria (i.e., BA) are extended in the lean phenotype $Atg7^{\Delta CD11c}$ mice. The administration of BA results in the activation of fat oxidation through the bile acid-TGR5-PPARα axis in adipose tissue, resulting in high energy consumption.

At the same time, BA activates visceral DPP-4, followed by the increase in GLP-1, thereby contributing to glucose homeostasis. Bile acids, cholate and taurine contributed to GLP-1 activity through a TGR5 receptor and improved insulin sensitivity.

Accordingly, it can be understood that BA plays an important role in the prevention or treatment of metabolic diseases such as diabetes and obesity (FIG. 7).

---

---

The invention claimed is:

1. A method for treating diabetes in a subject, the method comprising administering a pharmaceutically effective amount of *Bacteroides acidifaciens* to the subject in need of treatment of diabetes.

2. A method for treating diabetes according to claim 1, wherein the *Bacteroides acidifaciens* activates fat oxidation in adipose tissue, inhibits the activity of intestinal DPP-4 (dipeptidal peptidase-4), and increases GLP-1.

* * * * *

```
                        SEQUENCE LISTING

<160> NUMBER OF SEQ ID NOS: 3

<210> SEQ ID NO 1
<211> LENGTH: 52
<212> TYPE: DNA
<213> ORGANISM: Artificial Sequence
<220> FEATURE:
<223> OTHER INFORMATION: Primer 9F

<400> SEQUENCE: 1
cctatcccct gtgtgccttg gcagtctcag acagagtttg atcmtggctc ag            52

<210> SEQ ID NO 2
<211> LENGTH: 30
<212> TYPE: DNA
<213> ORGANISM: Artificial Sequence
<220> FEATURE:
<223> OTHER INFORMATION: Primer 541R; primer sequence portion appearing
      before barcode

<400> SEQUENCE: 2
ccatctcatc cctgcgtgtc tccgactcag                                     30

<210> SEQ ID NO 3
<211> LENGTH: 19
<212> TYPE: DNA
<213> ORGANISM: Artificial Sequence
<220> FEATURE:
<223> OTHER INFORMATION: Primer 541R; primer sequence portion appearing
      after barcode

<400> SEQUENCE: 3
acattaccgc ggctgctgg                                                 19
```